(12) United States Patent
Kanai et al.

(10) Patent No.: US 10,188,671 B2
(45) Date of Patent: Jan. 29, 2019

(54) BORON-DIPYRRIN COMPLEX AND MEDICAMENT CONTAINING THE SAME

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Yusuke Shimizu, Shinagawa-ku (JP); Atsuhiko Taniguchi, Hachioji (JP); Kounosuke Oisaki, Bunkyo-ku (JP); Yoichiro Kuninobu, Fukuoka (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 15/555,721

(22) PCT Filed: Mar. 4, 2016

(86) PCT No.: PCT/JP2016/056803
§ 371 (c)(1),
(2) Date: Sep. 5, 2017

(87) PCT Pub. No.: WO2016/143699
PCT Pub. Date: Sep. 15, 2016

(65) Prior Publication Data
US 2018/0042948 A1    Feb. 15, 2018

(30) Foreign Application Priority Data
Mar. 6, 2015 (JP) .................. 2015-044839

(51) Int. Cl.
| | | |
|---|---|---|
| A61K 31/69 | (2006.01) | |
| C07F 5/02 | (2006.01) | |
| A61P 25/28 | (2006.01) | |
| A61P 3/10 | (2006.01) | |
| A61P 25/16 | (2006.01) | |
| C07D 401/14 | (2006.01) | |
| C07D 455/04 | (2006.01) | |
| C07D 207/44 | (2006.01) | |
| C07D 207/456 | (2006.01) | |
| A61K 31/4025 | (2006.01) | |
| A61K 31/4725 | (2006.01) | |
| C07D 207/46 | (2006.01) | |
| C07D 215/06 | (2006.01) | |
| A61K 41/00 | (2006.01) | |

(52) U.S. Cl.
CPC .......... *A61K 31/69* (2013.01); *A61K 31/4025* (2013.01); *A61K 31/4725* (2013.01); *C07D 207/44* (2013.01); *C07D 207/456* (2013.01); *C07D 207/46* (2013.01); *C07D 215/06* (2013.01); *C07D 401/14* (2013.01); *C07D 455/04* (2013.01); *C07F 5/02* (2013.01); *A61K 41/00* (2013.01)

(58) Field of Classification Search
CPC ....................................................... C07F 5/02
See application file for complete search history.

(56) References Cited

U.S. PATENT DOCUMENTS

| | | |
|---|---|---|
| 4,774,339 A | 9/1988 | Haugland et al. |
| 2009/0233373 A1 | 9/2009 | Hamachi et al. |
| 2011/0287473 A1 | 11/2011 | De Barry et al. |
| 2015/0158841 A1 | 6/2015 | Ran et al. |

FOREIGN PATENT DOCUMENTS

| | | |
|---|---|---|
| JP | 2009-280567 A | 12/2009 |
| JP | 2012-513973 A | 6/2012 |
| WO | WO 2008/093251 A1 | 9/2008 |
| WO | WO 2010/125907 A1 | 11/2010 |
| WO | WO 2014/025806 A1 | 2/2014 |
| WO | WO 2014/182704 A2 | 11/2014 |
| WO | WO 2014/182704 A3 | 11/2014 |
| WO | WO 2016/010092 A1 | 1/2016 |

OTHER PUBLICATIONS

International Search Report dated May 31, 2016 in PCT/JP2016/056803 filed Mar. 4, 2016.

Ismael J. Arroyo, et al., "The Smallest and One of the Brightest, Efficient Preparation and Optical Description of the Parent Borondipyrromethane System" J. Org. Chem., vol. 74, No. 15, 2009, pp. 5719-5722.

Anvita Srivastava, et al., "Identifying the Bond Responsible for the Fluorescence Modulation in an Amyloid Fibril Sensor" Chemistry—A European Journal, vol. 16, 2010, pp. 9257-9263.

Atsuhiko Taniguchi et al., "Attenuation of the Aggregation and Neurotoxicity of Amyloid-β Peptides by Catalytic Photooxygenation" Angewandte Chemie International Edition, vol. 53, 2014, pp. 1382-1385.

(Continued)

*Primary Examiner* — Susanna Moore
(74) *Attorney, Agent, or Firm* — Oblon, McClelland, Maier & Neustadt, L.L.P.

(57) ABSTRACT

Provided is a compound which is useful as an in vivo applicable, amyloid-oxygenating catalyst selective for amyloid and applicable not only to an Aβ peptide, but also to other amyloids and a drug containing the compound for preventing and/or treating amyloid-related diseases. Disclosed is a boron-dipyrrin complex represented by the following formula (1)

(1)

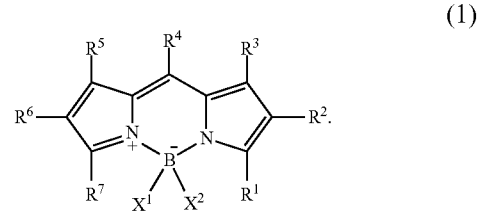

10 Claims, 11 Drawing Sheets

(56) References Cited

OTHER PUBLICATIONS

Liming Hou, et al., "Methlonine 35 Oxidation Reduces Fibril Assembly of the Amyloid Aβ-(1-42) Peptide of Alzheimer's Disease" The Journal of Biological Chemistry, vol. 277, No. 43, 2002, 5 Pages.

Gal Bitan, et al., "A Molecular Switch in Amyloid Assembly: Met and Amyloid β-Protein Oligomerization" J. Am. Chem. Soc., vol. 125, No. 50, 2003, pp. 15359-15365.

Jackob Moskovitz, et al., "Induction of Methionine-Sulfoxide Reductases Protects Neurons from Amyloid β-Protein Insults in Vitro and in Vivo" Biochemistry, vol. 50, 2011, pp. 10687-10697.

[Figure 1]
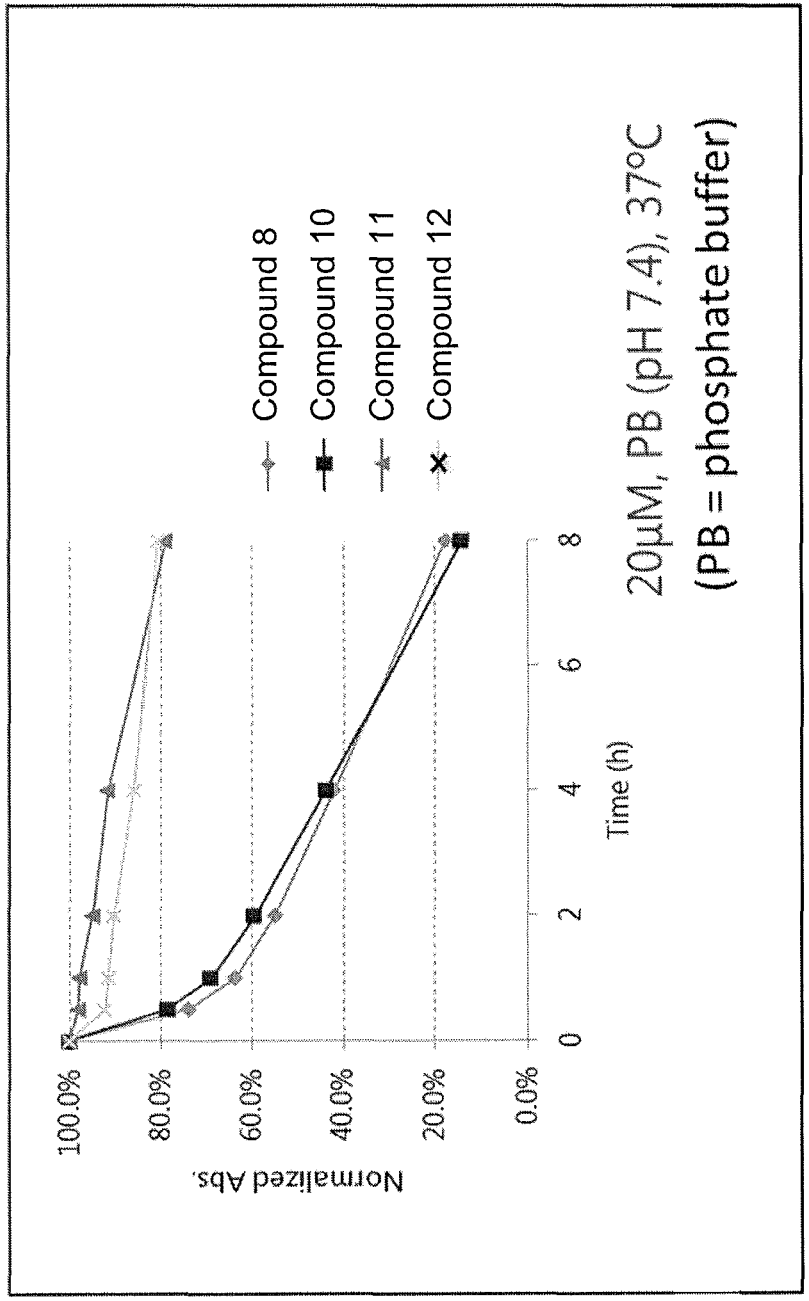

[Figure 2]
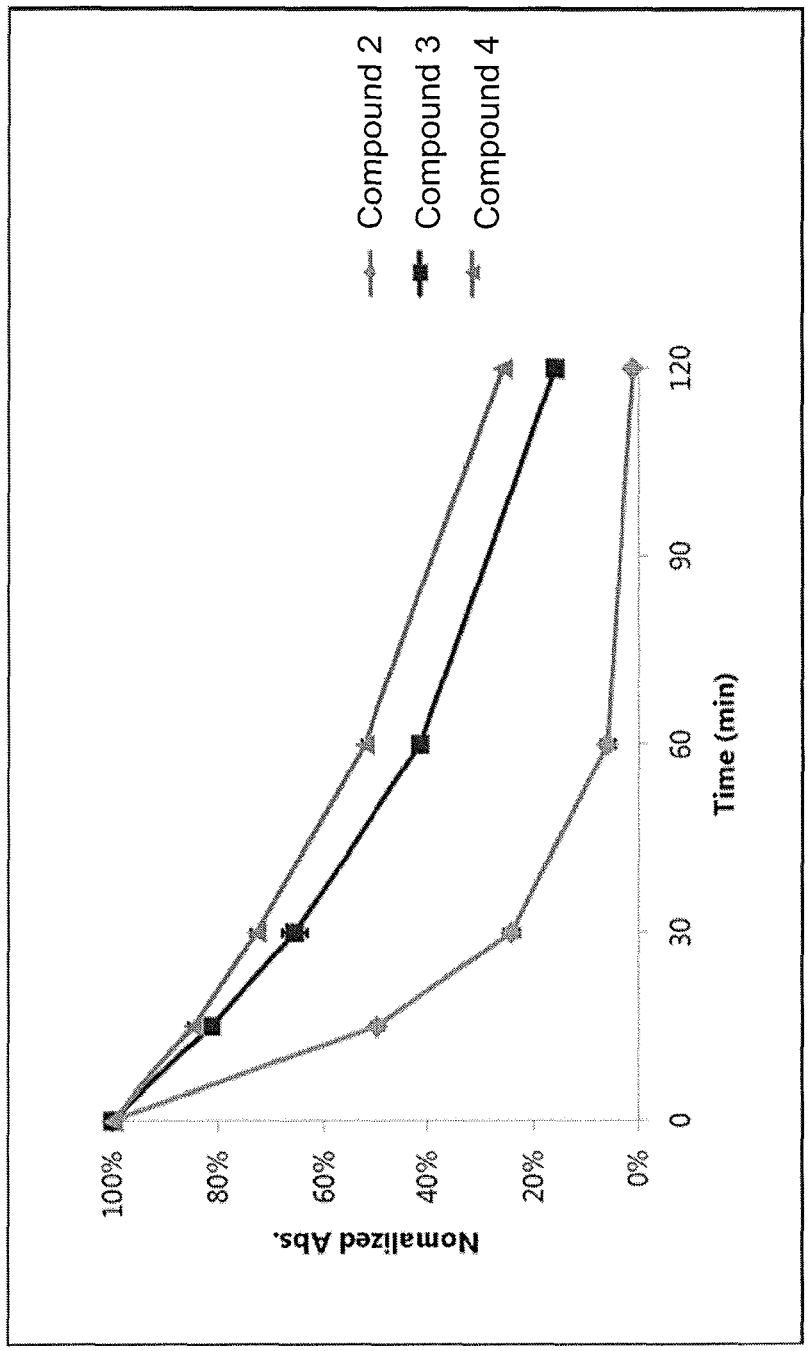

[Figure 3]
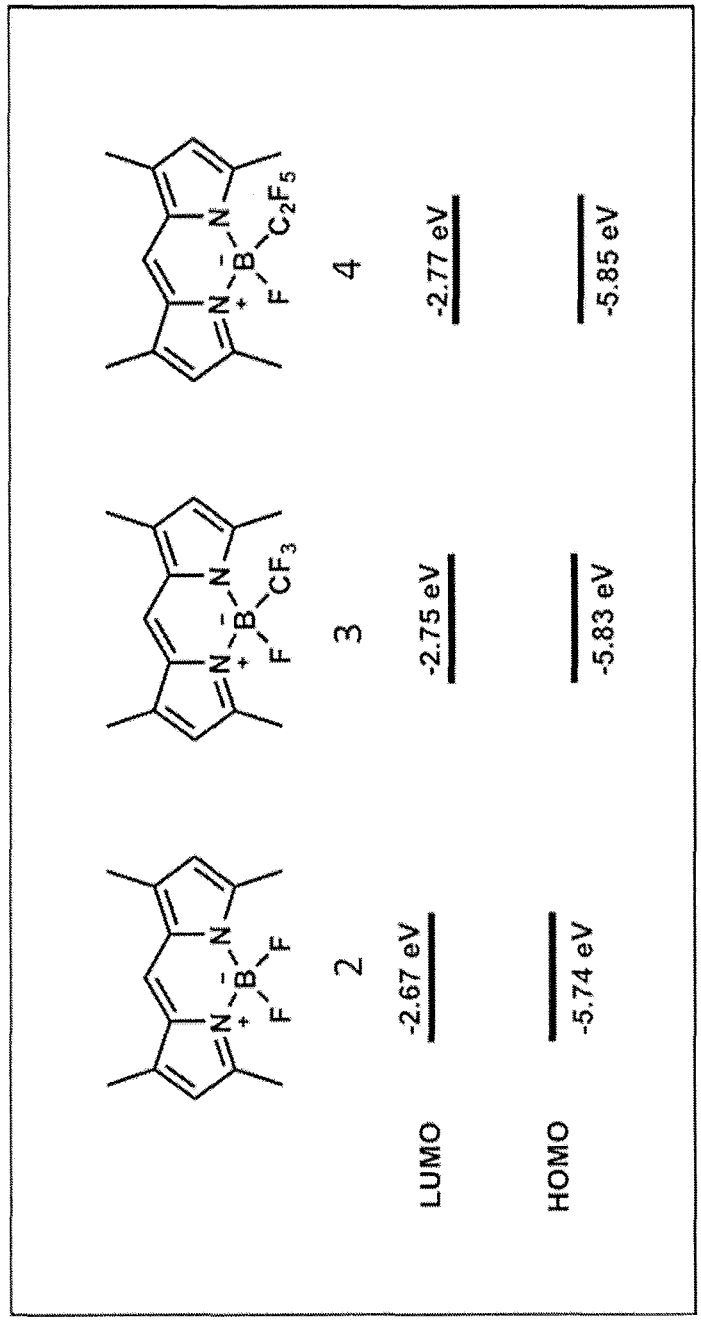

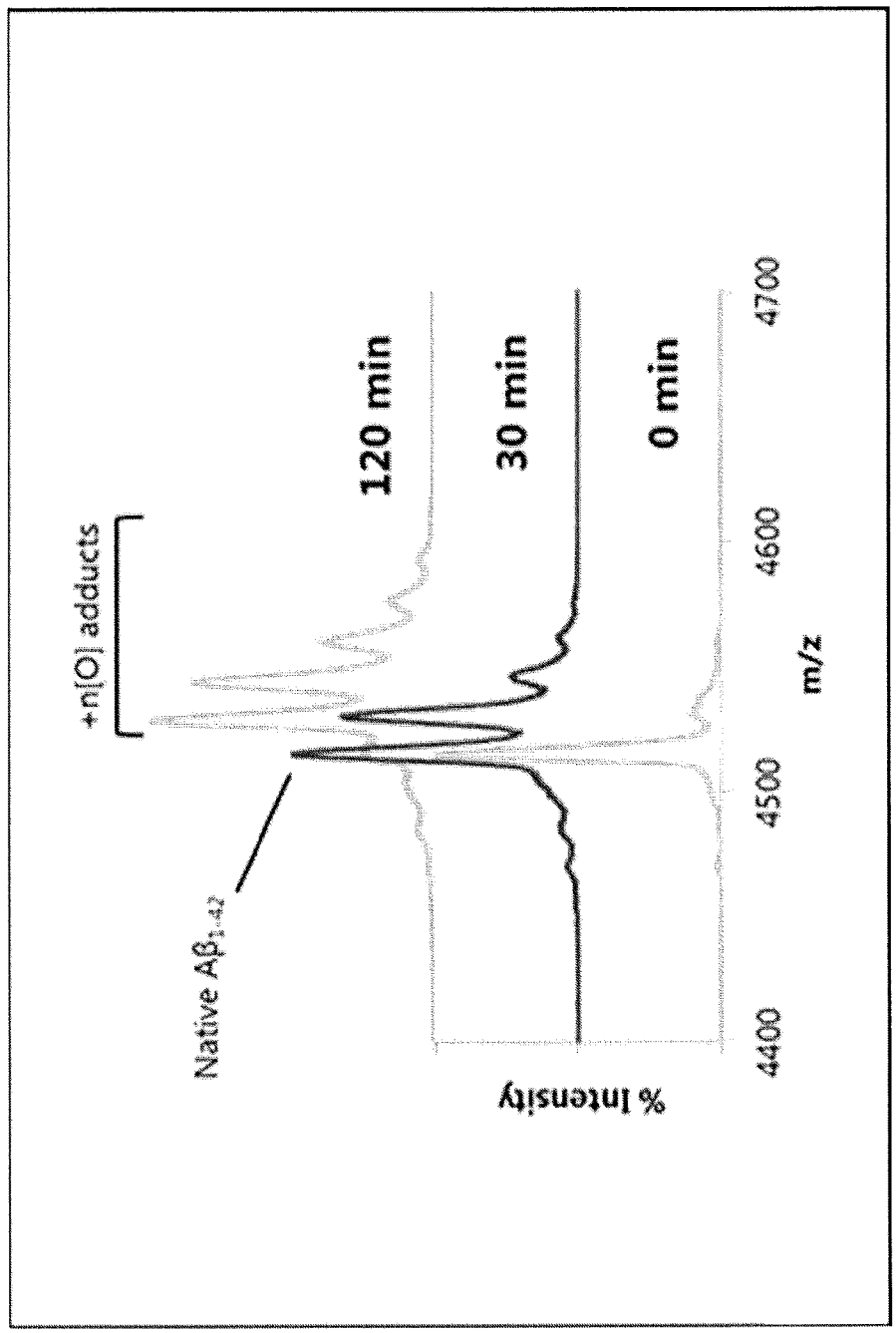
[Figure 4]

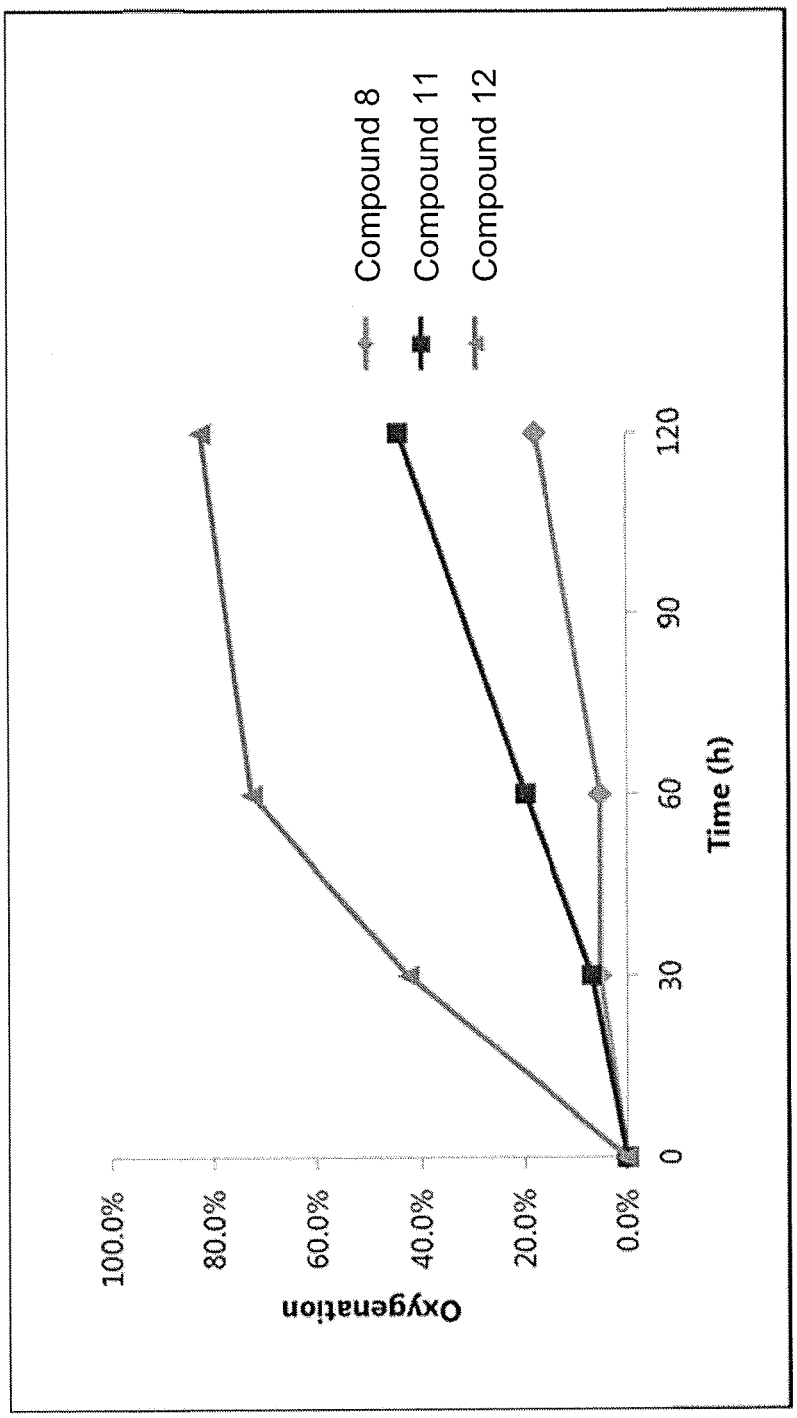
[Figure 5]

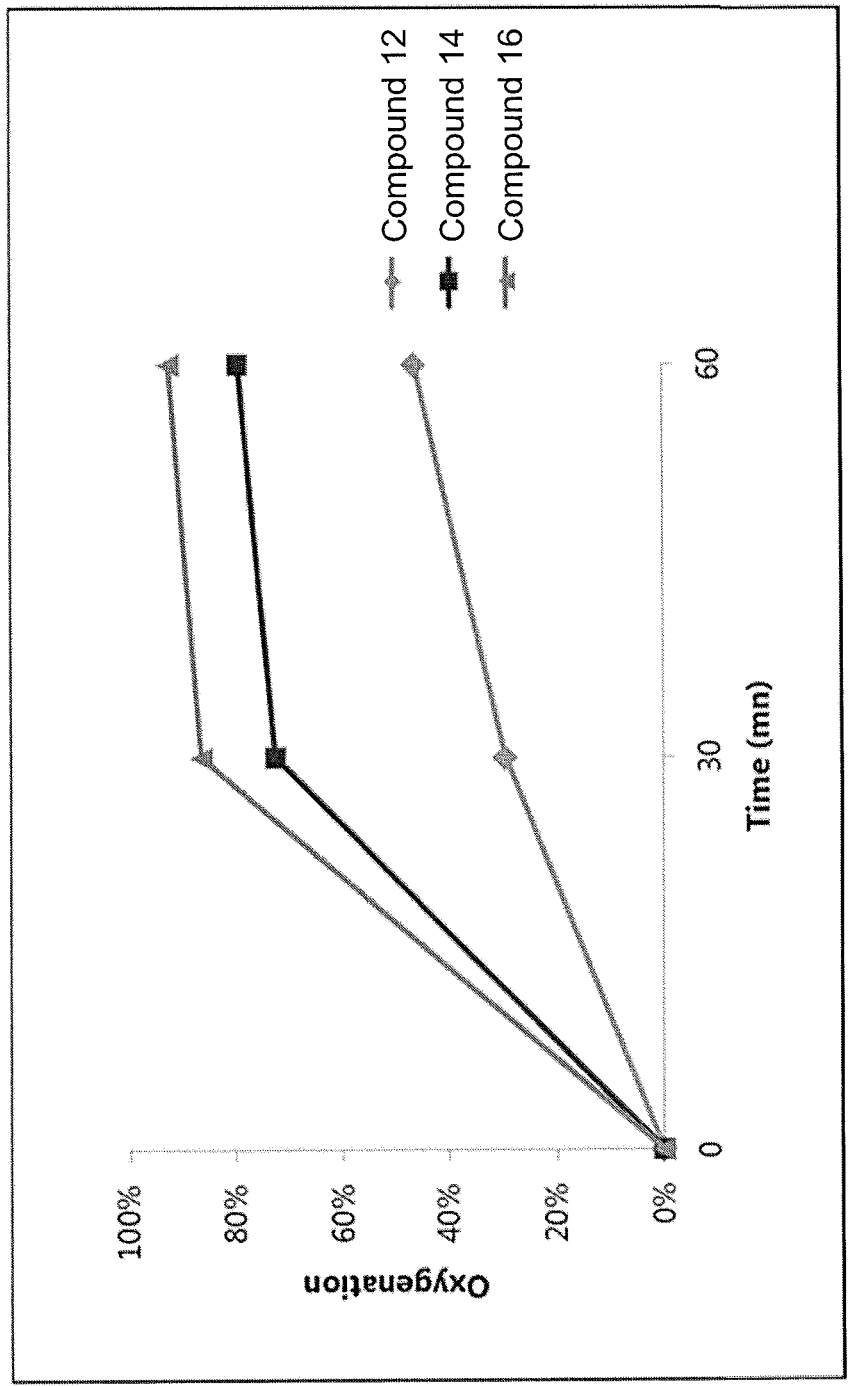
[Figure 6]

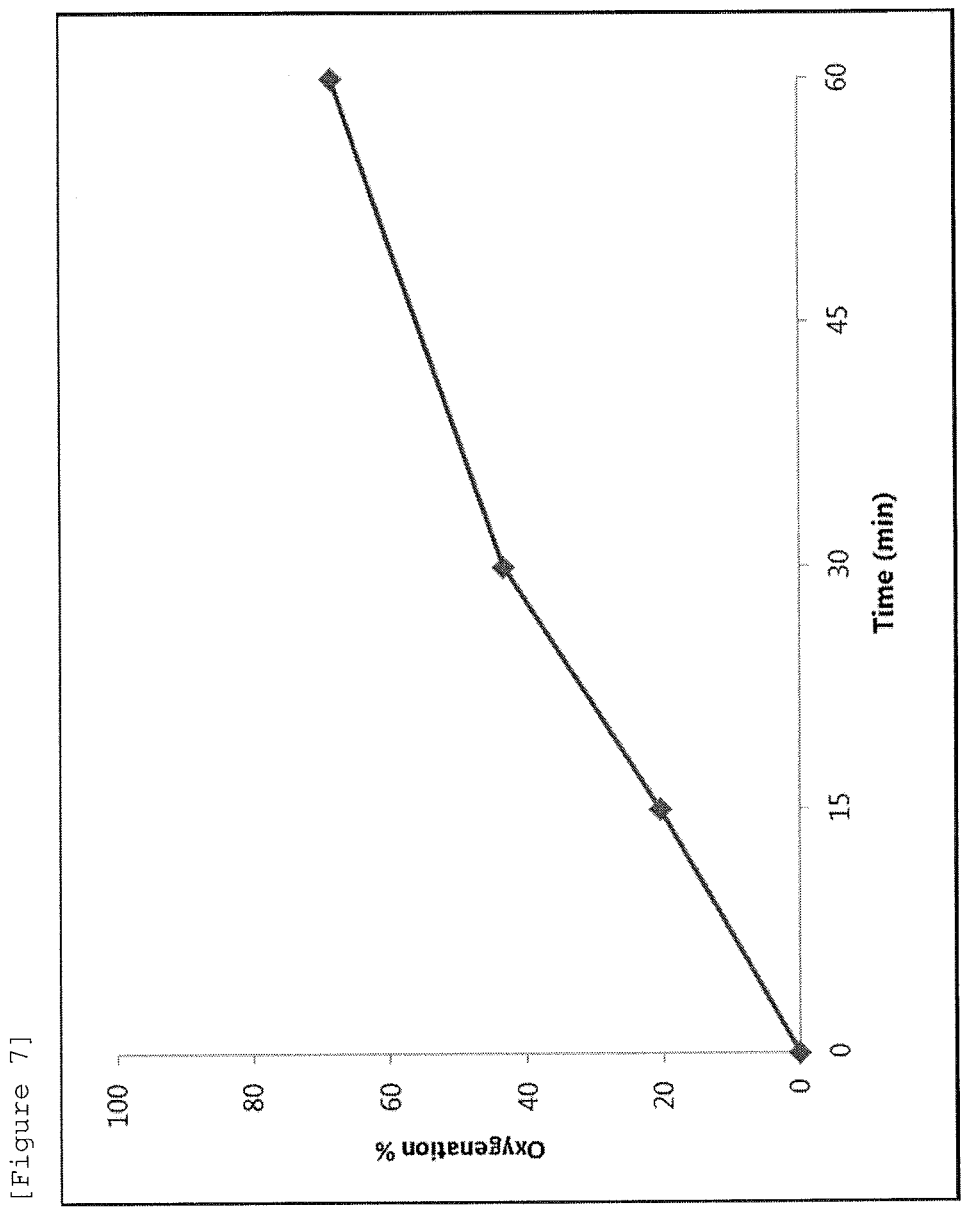
[Figure 7]

[Figure 8]
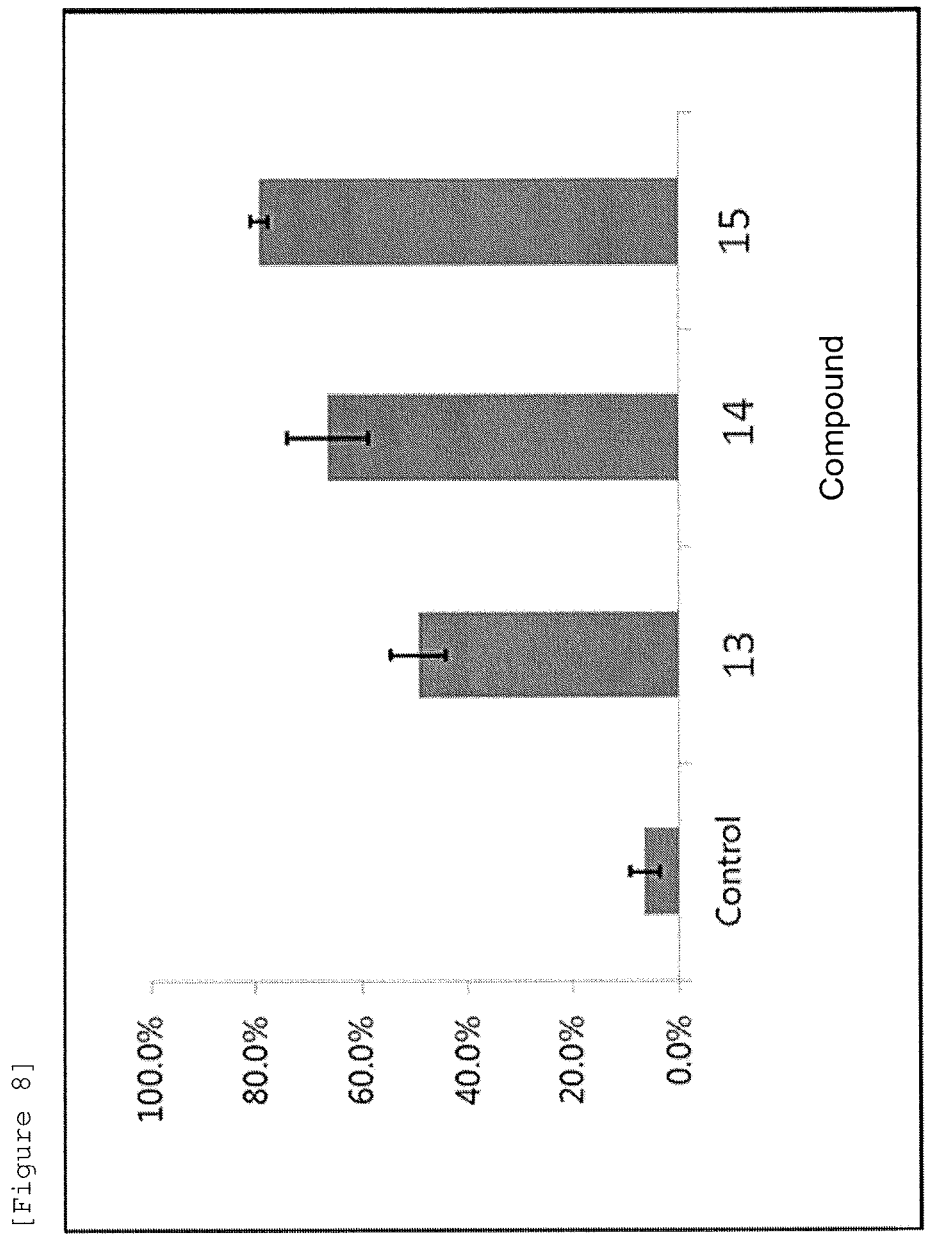

[Figure 9]
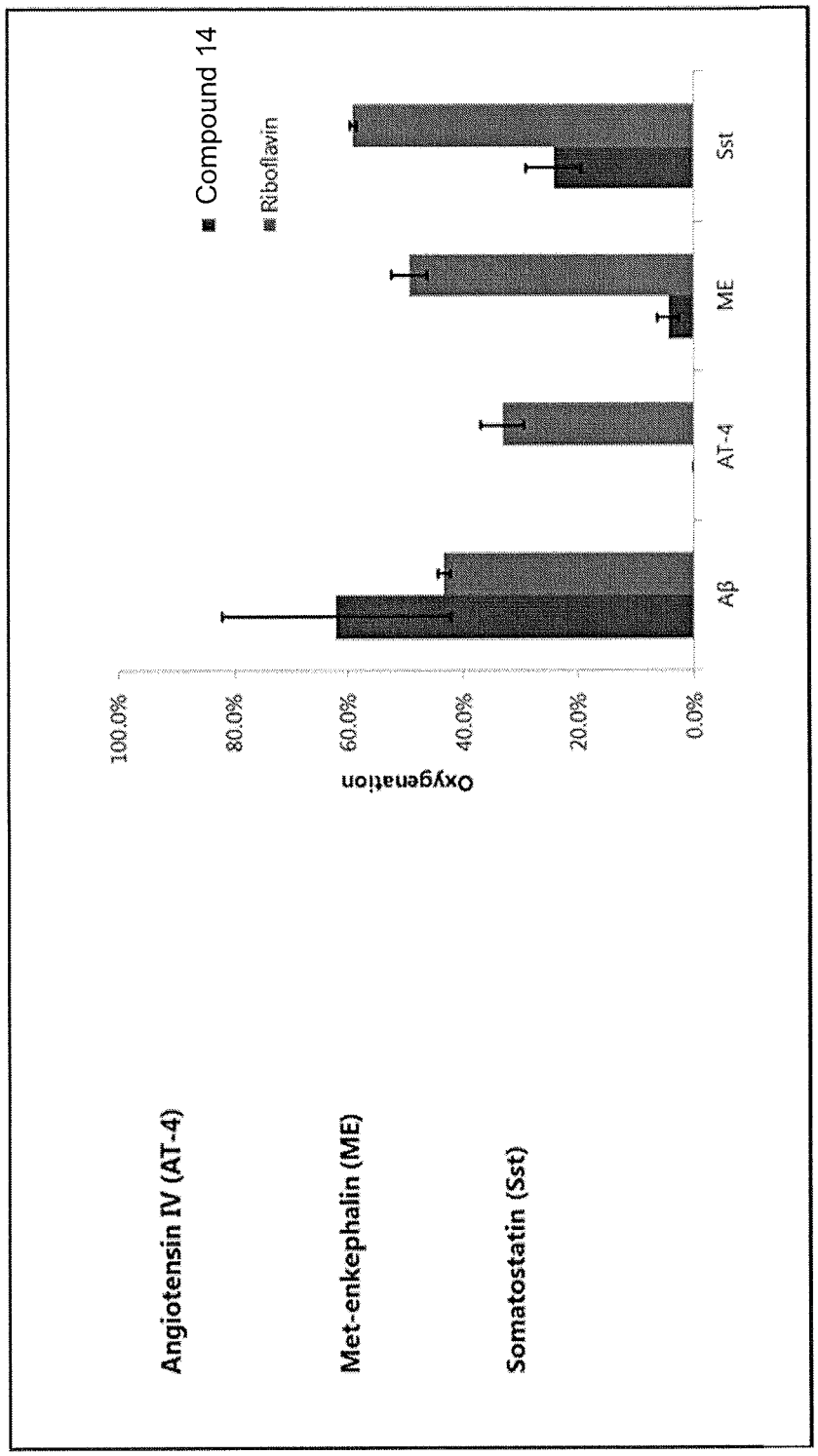

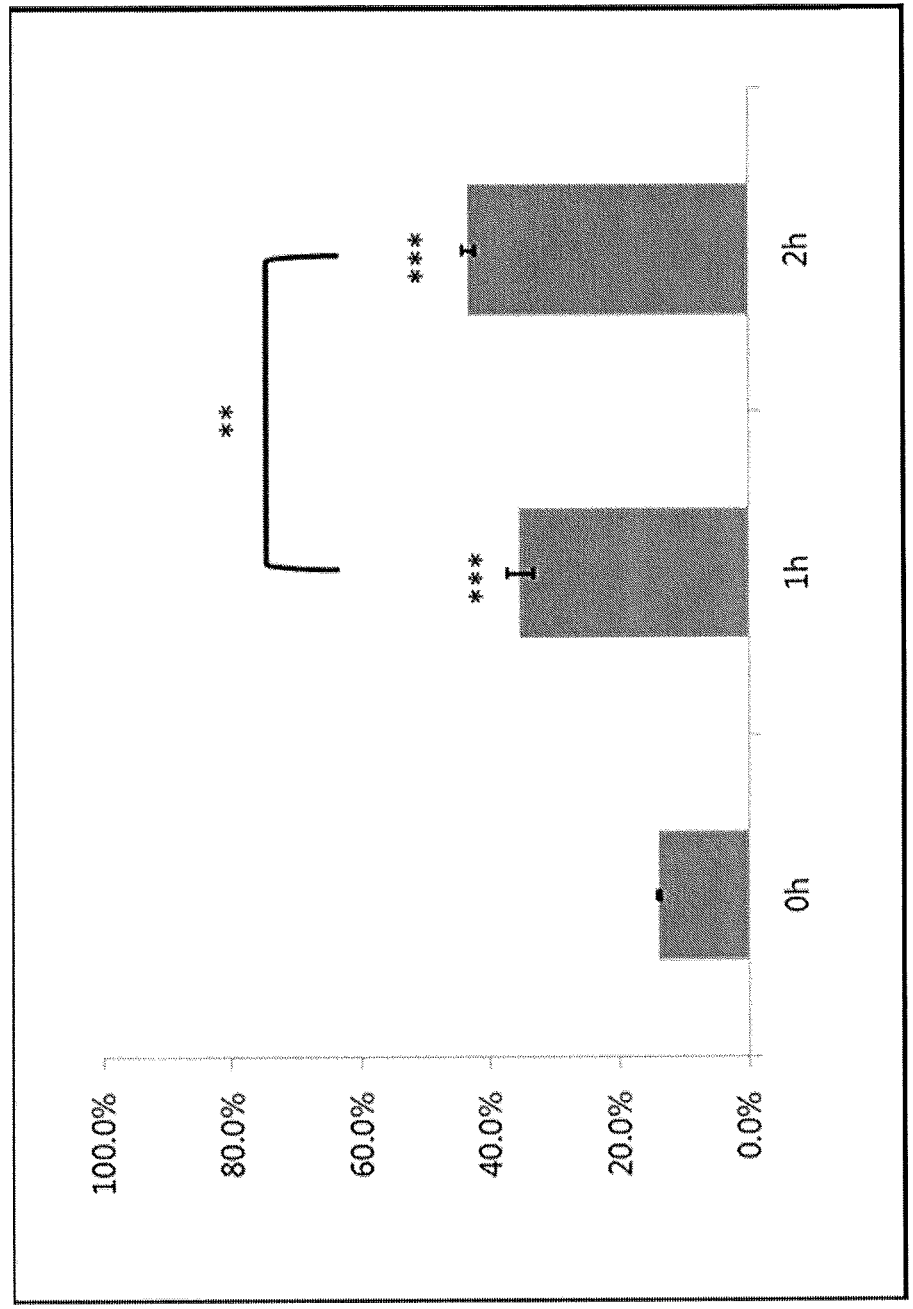
[Figure 10]

[Figure 11]
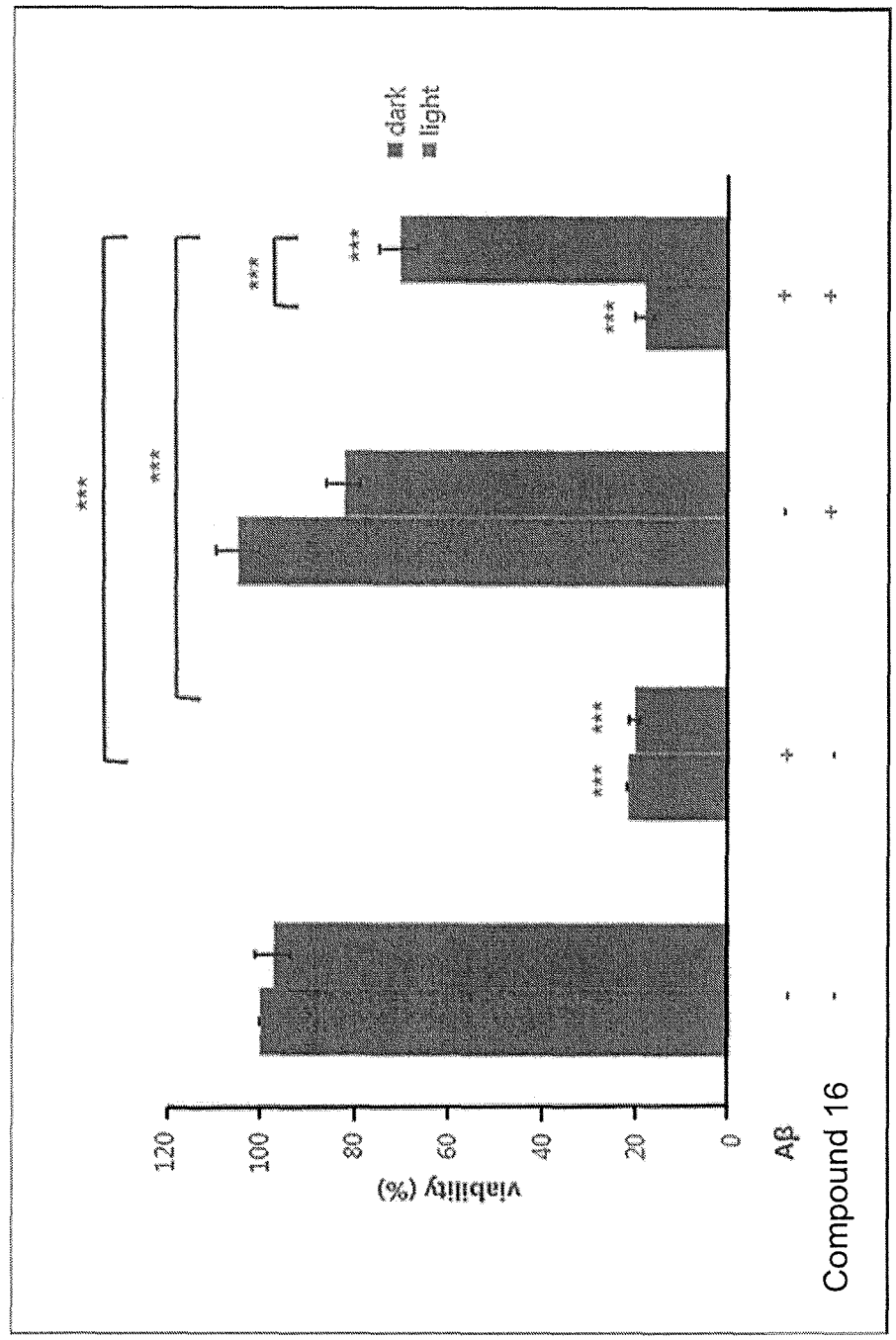

BORON-DIPYRRIN COMPLEX AND MEDICAMENT CONTAINING THE SAME

TECHNICAL FIELD

The present invention relates to medicaments for preventing or treating diseases involving a pathogenic amyloid.

BACKGROUND ART

Usually, proteins are each folded to form the specific native structure thereof, thereby exerting biological functions. When the proteins are misfolded, however, they may aggregate to form β-sheet-rich fibers (i.e., to form amyloid). Aggregates (e.g., oligomers, proto-fibrils, fibers) produced through this amyloid formation are known to cause various dysfunctions (these disorders are generally referred to as "amyloid diseases"). Here, 20 or more proteins have been identified as substances responsible for the amyloid diseases. Example of such amyloid known include: amyloid β, tau protein in Alzheimer's disease; α-synuclein in Parkinson's disease; amylin in diabetes mellitus; transthyretin in systemic amyloidosis; and huntingtin in Huntington's disease.

For example, as for amyloid β (abbreviated to Aβ), which is a causative amyloid of Alzheimer's disease, inhibitors of enzymes mediating the production of Aβ from a precursor protein, promoters of Aβ-degrading enzymes, immunotherapy, Aβ aggregation inhibitors, and the like are known as strategies to develop therapeutic drugs targeting these pathogenic amyloids.

On the other hand, it has been reported as to Aβ that a Met-oxidized form of an Aβ peptide (the sulfur atom of the Met residue is oxidized to sulfoxide (—S═O—)) remains in a small amount in vivo, and the Met-oxidized form is less aggregable as compared with the native Aβ peptide (Non Patent Literatures 1 to 3). From these viewpoints, the present inventors reported that oxidized forms of Aβ peptides are obtained by the oxidation of the Aβ peptides using a flavin photocatalyst having an Aβ-binding site represented by the formula (a), and these oxidized forms of Aβ peptides suppress the aggregation of Aβ (Non Patent Literature 4).

CITATION LIST

Non Patent Literature

[Non Patent Literature 1] Hou, L. et al. J. Biol. Chem., 2002, Vol. 277, No. 43, p 40173-40176

[Non Patent Literature 2] Bitan, G. et al. J. Am. Chem. Soc., 2003, Vol. 125, No. 50, p 15359-15365

[Non Patent Literature 3] Moskovitz, J. et al. Biochemistry, 2011, 50, p 10687-10697

[Non Patent Literature 4] A. Taniguchi et al. Angew. Chem. Int. Ed., 2034, 53, 1382-1385

SUMMARY OF INVENTION

Technical Problem

The flavin photocatalyst used in Non Patent Literature 4 described above, however, has oxidative activity even in the absence of Aβ. This flavin photocatalyst might therefore react nonspecifically in vivo and has thus been difficult to apply in vivo, though applicable in vitro. In addition, the flavin photocatalyst could be applied only to Aβ peptides.

Thus, an object of the present invention is to provide: a compound useful as an amyloid oxidation catalyst which is applicable in vivo, is selective to amyloids and is applicable not only to Aβ peptides but to other amyloids; and a prophylactic or therapeutic drug for an amyloid-related disease, comprising the same.

Solution to Problem

Accordingly, the present inventors conducted various studies to develop a catalyst which has selective oxidative activity against amyloids and is applicable in vivo, and consequently completed the present invention by finding that a boron-dipyrrin complex, which is represented by the following formula (1), having a halogen atom or a halogenoalkyl group on the boron atom exhibits strong oxygenation activity on an Aβ peptide and other amyloids; the complex exhibits particularly strong oxygenation activity on very toxic Aβ peptide aggregates; the complex exhibits little oxygenation activity on peptides other than amyloid; and the complex is highly stable in water and/or under light irradiation, and that the boron-dipyrrin complex represented by the following formula (1) is useful as an in vivo catalyst which yields oxidized forms of amyloids having no aggregability.

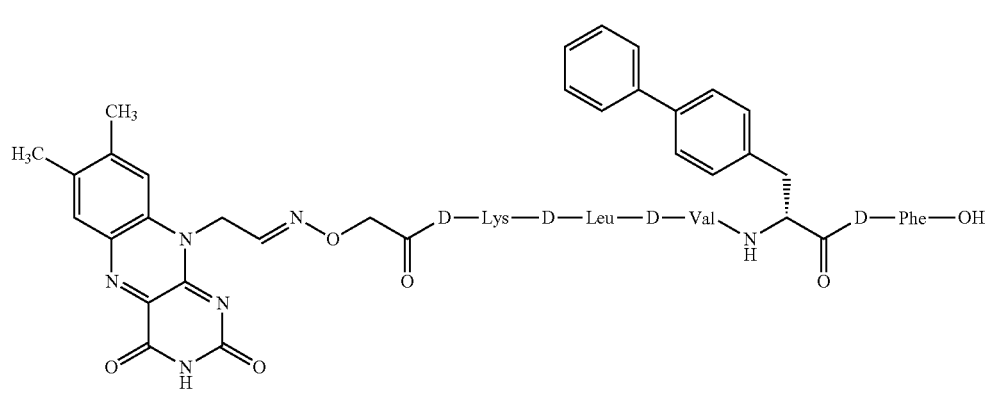

(a)

Further, a portion of the boron-dipyrrin complex represented by the following formula (1) (wherein $R^1$ is hydrogen or alkyl) emits strong fluorescence upon light irradiation and is very stable in water and/or under light irradiation conditions. Thus, the portion is found to be useful as a fluorescent dye in vivo and/or in tissues or as an intermediate for the manufacture of the compound represented by formula (1). In this way, the present inventors have completed the present invention.

Specifically, the present invention provides the following items [1] to [13].

[1] A boron-dipyrrin complex represented by the following formula (1):

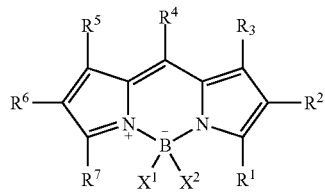

(1)

wherein $X^1$ and $X^2$ are the same or different and each represent a halogenoalkyl group or a halogen atom;

$R^1$ represents a hydrogen atom, an alkyl group, or a group represented by formula (b):

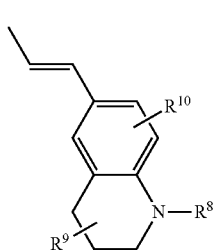

(b)

$R^2$ and $R^6$ are the same or different and each represent a hydrogen atom or a halogen atom;

$R^3$, $R^4$, $R^5$, and $R^7$ are the same or different and each represent a hydrogen atom, a halogen atom, or an alkyl group;

$R^8$ represents a hydrogen atom or —$(CH_2)_l$—$(Y)_m$—$(CH_2)_n$—Z wherein Y represents —CO—, —COHN—, or a triazole ring, Z represents a carboxyl group, a sulfonic acid group, or a —CO-peptide residue, l and n each represent an integer of 1 to 6, and m represents 0 or 1;

$R^9$ and $R^{10}$ are the same or different and each represent a hydrogen atom, an alkyl group, an alkoxy group, a halogen atom, an amino group, a nitro group, or a cyano group; and $R^8$ and $R^{10}$ optionally together form an alkylene group.

[2] The boron-dipyrrin complex according to item [1], wherein $X^1$ and $X^2$ are the same or different and are each a fluoro $C_1$-$C_4$ alkyl group or a halogen atom.

[3] The boron-dipyrrin complex according to item [1] or [2], wherein one of $R^2$ and $R^6$ is a halogen atom and the other is a hydrogen atom or a halogen atom.

[4] The boron-dipyrrin complex according to any one of items [1] to [3], wherein $R^1$ is the group represented by formula (b).

[5] A boron-dipyrrin complex represented by the following formula (1A):

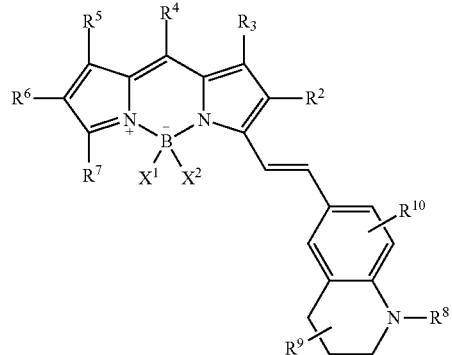

(1A)

wherein $X^1$ and $X^2$ are the same or different and each represent a halogenoalkyl group or a halogen atom;

one of $R^2$ and $R^6$ represents a halogen atom and the other represents a hydrogen atom or a halogen atom;

$R^3$, $R^4$, $R^5$, and $R^7$ are the same or different and each represent a hydrogen atom, a halogen atom, or an alkyl group;

$R^8$ represents a hydrogen atom or —$(CH_2)_l$—$(Y)_m$—$(CH_2)_n$—Z wherein Y represents —CO—, —CONH—, or a triazole ring, Z represents a carboxyl group, a sulfonic acid group, or a —CO-peptide residue, l and n each represent an integer of 1 to 6, and m represents 0 or 1;

$R^9$ and $R^{10}$ are the same or different and each represent a hydrogen atom, an alkyl group, an alkoxy group, a halogen atom, an amino group, a nitro group, or a cyano group; and $R^8$ and $R^{10}$ together optionally form an alkylene group.

[6] The boron-dipyrrin complex according to item [5], wherein $X^1$ and $X^2$ are the same or different and are each a fluoro $C_1$-$C_4$ alkyl group or a halogen atom.

[7] The boron-dipyrrin complex according to item [5] or [6], wherein one of $R^2$ and $R^6$ is a halogen atom and the other is a hydrogen atom or a halogen atom.

[8] A medicament comprising, as an active ingredient, the boron-dipyrrin complex according to any one of items [5] to [7].

[9] The medicament according to item [8], which is a drug for preventing or treating a disease involving a pathogenic amyloid.

[10] A pharmaceutical composition comprising: the boron-dipyrrin complex according to any one of items [5] to [7]; and a pharmaceutically acceptable carrier.

[11] Use of the boron-dipyrrin complex according to any one of items [5] to [7] for the manufacture of a drug for preventing or treating a disease involving a pathogenic amyloid.

[12] The boron-dipyrrin complex according to any one of items [5] to [7] for preventing or treating a disease involving a pathogenic amyloid.

[13] A method for preventing or treating a disease involving a pathogenic amyloid, comprising administering an effective amount of the boron-dipyrrin complex according to any one of items [5] to [7].

Effects of Invention

A boron-dipyrrin complex (1A) of the present invention has increased catalytic activity in which a pathogenic amyloid such as an Aβ peptide is oxygenated. The complex can inhibit amyloid aggregation through amyloid oxygenation in vivo. In addition, the complex has increased oxygenation activity on aggregated amyloid. The complex exhibits little oxygenation activity on peptides other than amyloid. Further, the complex is very stable in water and/or under light irradiation conditions. Thus, the complex is useful as a drug for preventing or treating a disease involving a pathogenic amyloid. Moreover, a compound represented by formula (1) wherein $R^1$ is a hydrogen atom or an alkyl group is useful as a fluorescent dye for in vivo and/or tissue staining. As used herein, the term "oxygenation" means, among oxidation reactions, a specific reaction in which an oxygen atom is bonded.

BRIEF DESCRIPTION OF DRAWINGS

FIG. 1 shows the water stability of each of compounds of the present invention.

FIG. 2 shows the stability under a light irradiation condition of compounds of the present invention.

FIG. 3 shows the results of calculating HOMO/LUMO levels.

FIG. 4 illustrates the results of mass spectroscopy after an $A\beta_{1-42}$ peptide was oxygenated.

FIG. 5 shows the Aβ peptide-oxygenating activity of compounds of the present invention.

FIG. 6 shows the Aβ peptide-oxygenating activity of compounds of the present invention.

FIG. 7 shows the Aβ peptide-oxygenating activity of a compound of the present invention.

FIG. 8 shows the Aβ peptide-oxygenating activity of compounds of the present invention.

FIG. 9 illustrates how the Aβ peptide-oxygenating activity of a compound of the present invention is selective for peptides.

FIG. 10 shows the activity of a compound of the present invention to oxygenate aggregated Aβ peptides.

FIG. 11 illustrates how a compound of the present invention affected cells by selectively oxygenating $A\beta_{1-42}$.

DESCRIPTION OF EMBODIMENTS

In formula (1), $X^1$ and $X^2$ are the same or different and each represent a halogenoalkyl group or a halogen atom. As the halogenoalkyl group, a halogeno $C_1$-$C_4$ alkyl group is preferable, and a fluoro $C_1$-$C_4$ alkyl group is particularly preferable. Specific examples of the more preferable halogenoalkyl group include perfluoro $C_1$-$C_4$ alkyl groups such as a trifluoromethyl group, a pentafluoroethyl group, and a heptafluoropropyl group. Examples of the halogen atom include a fluorine atom, a chlorine atom, a bromine atom, and an iodine atom, and a fluorine atom is preferable.

$X^1$ and $X^1$ may both be halogen atoms or halogenoalkyl groups, but preferably, $X^1$ is a halogenoalkyl group and $X^2$ is a halogen atom; more preferably, $X^1$ is a perfluoro $C_1$-$C_4$ alkyl group and $X^2$ is a fluorine atom; and further preferably, $X^1$ is a trifluoromethyl group or a pentafluoroethyl group and $X^2$ is a fluorine atom.

In formula (1), $R^1$ represents a hydrogen atom, an alkyl group, or a group represented by formula (b):

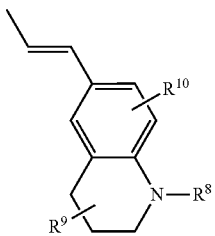

In formula (b), $R^8$ represents a hydrogen atom or —$(CH_2)_l$—$(Y)_m$—$(CH_2)_n$—Z wherein Y represents —CO—, —COHN—, or a triazole ring, Z represents a carboxyl group, a sulfonic acid group, or a —CO-peptide residue, l and n each represent an integer of 1 to 6, and m represents 0 or 1;

$R^9$ and $R^{10}$ are the same or different and each represent a hydrogen atom, an alkyl group, an alkoxy group, a halogen atom, an amino group, a nitro group, or a cyano group; and $R^8$ and $R^{10}$ together optionally form an alkylene group.

The alkyl group represented by $R^1$ is preferably a $C_1$-$C_6$ alkyl group. Specific examples include linear or branched $C_1$-$C_4$ alkyl groups such as a methyl group, an ethyl group, a n-propyl group, an isopropyl group, a n-butyl group, an isobutyl group, and a tert-butyl group. Among them, a methyl group is particularly preferable.

$R^2$ and $R^6$ are the same or different and each represent a hydrogen atom or a halogen atom. Preferably, one of $R^2$ and $R^6$ represents a halogen atom and the other represents a hydrogen atom or a halogen atom. Here, examples of the halogen atom include a fluorine atom, a chlorine atom, a bromine atom, and an iodine atom, and a bromine atom or an iodine atom is more preferable, and an iodine atom is further preferable.

At least one of $R^2$ and $R^6$ may be a halogen atom. In this case, irradiation of light with a long wavelength of 640 nm or more causes strong oxygenation activity on amyloid, in particular, aggregated amyloid. Stability to water and stability under light irradiation conditions are both good.

$R^3$, $R^4$, $R^5$, and $R^7$ are the same or different and each represent a hydrogen atom, a halogen atom, or an alkyl group. Here, examples of the halogen atom include a fluorine, chlorine, bromine, and iodine atom. Examples of the alkyl group include a $C_1$-$C_{12}$ alkyl group, and a $C_1$-$C_6$ alkyl group is preferable. Examples of the alkyl group include linear or branched alkyl groups such as a methyl group, an ethyl group, a n-propyl group, an isopropyl group, and a n-butyl group.

$R^3$, $R^5$, and $R^7$ are each preferably a hydrogen atom, a halogen atom, or a $C_1$-$C_6$ alkyl group, and more preferably a hydrogen atom or a $C_1$-$C_6$ alkyl group. In addition, $R^4$ is preferably a hydrogen atom. Notably, it is preferable that $R^1$ and $R^7$ not be hydrogen atoms simultaneously.

$R^8$ represents a hydrogen atom or —$(CH_2)_l$—$(Y)_m$—$(CH_2)_n$—Z. Here, Y represents —CO—, —COHN—, or a triazole ring. Examples of the triazole ring include a 1,2,3-triazole-1,4-diyl group and a 1,2,4-triazole-1,3-diyl group. Z represents a carboxyl group (—COOH), a sulfonic acid group (—SO$_3$H), or a —CO-peptide residue. Examples of the peptide of the —CO-peptide residue include oligopeptides, for example from a dipeptide to a hexapeptide. As the oligopeptides, oligopeptides containing 2 to 6 amino acids selected from Lys, Leu, Val, Phe, and modified amino acids thereof are preferable, oligopeptides containing 4 to 6 amino acids are more preferable, and a pentapeptide is further preferable. Examples of the modified amino acids include amino acids modified by a phenyl group, a halogenophenyl group, a naphthyl group, or the like. A phenyl group-modified amino acid is preferable. Specific examples of the oligopeptides include KLVFF, KLVF(4Ph)F, and KVLF(βPh)F. Here, these preferable oligopeptides exert activity to inhibit aggregation of Aβ. For example, the peptide KLVF(4Ph)F bonded to compound 19 is particularly preferable because of its excellent Aβ aggregation inhibitory activity (Non Patent Literature 4). l and n each represent an integer of 1 to 6, and are each preferably an integer of 2 to 6, m represents 0 or 1.

The alkylene group formed by $R^8$ and $R^{10}$ bonded together is preferably an alkylene group having 2 to 4 carbon atoms, and examples thereof include an ethylene group, a trimethylene group, and a tetramethylene group. Note that when $R^8$ and $R^{10}$ taken together form an alkylene group, the tetrahydroquinoline ring is preferably substituted at position 8 by the $R^{10}$.

$R^9$ and $R^{10}$ are the same or different and each represent a hydrogen atom, an alkyl group, an alkoxy group, a halogen atom, an amino group, a nitro group, or a cyano group. Here, as the alkyl group, a $C_1$-$C_6$ alkyl group is preferable and examples of the alkyl group include linear or branched $C_1$-$C_4$ alkyl groups such as a methyl group, an ethyl group, a n-propyl group, and an isopropyl group. The alkoxy group is preferably a $C_1$-$C_6$ alkoxy group, and examples thereof include a methoxy group, an ethoxy group, a n-propyloxy group, and isopropyloxy group. Examples of the halogen atom include a fluorine atom, a chlorine atom, a bromine atom, and an iodine atom.

Preferably, in formula (1), $X^1$ and $X^2$ are the same or different and are each a fluoro $C_1$-$C_4$ alkyl group or a halogen atom; $R^1$ is a hydrogen atom, a $C_{1-4}$ alkyl group, or a group represented by formula (b) (in formula (b), $R^8$ represents —$(CH_2)_l$—$(Y)_m$—$(CH_2)_n$—Z or $R^8$ and $R^{10}$ taken together form a $C_2$-$C_4$ alkylene group, and $R^9$ represents a hydrogen atom, a $C_1$-$C_6$ alkyl group, or a $C_1$-$C_6$ alkoxy group); at least one of $R^2$ and $R^6$ is a halogen atom and the other is a hydrogen atom or a halogen atom; and $R^3$, $R^4$, $R^5$, and $R^7$ are the same or different and is each a hydrogen atom, a $C_1$-$C_6$ alkyl group, or a halogen atom.

A compound in which $R^1$ is formula (b) is activated by irradiation of light with a long wavelength of 590 nm or more, has strong oxygenation activity on amyloid such as Aβ, is very stable in water and under light irradiation conditions, and is thus useful as an in vivo catalyst which helps generate nonaggregatable oxygenated amyloid. The compound is represented by the following formula (1A):

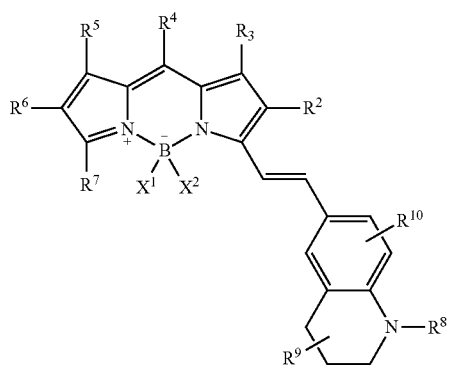

(1A)

(In the formula, $X^1$, $X^2$, $R^2$ to $R^{10}$ are the same as above.)

A compound in which $R^1$ is a hydrogen atom or an alkyl group emits strong fluorescence and is thus useful as a fluorescent dye which emits fluorescence to stain a living body, tissues, cells, etc. The compound is represented by the following formula (1B):

(1B)

(In the formula, $R^{1a}$ represents a hydrogen atom or an alkyl group and $X^1$, $X^2$, $R^2$ to $R^7$ are the same as above.)

Preferably, in formula (1A), $X^1$ and $X^2$ are the same or different and are each a fluoro $C_1$-$C_4$ alkyl group or a halogen atom; $R^8$ represents —$(CH_2)_l$—$(Y)_m$—$(CH_2)_n$—Z or $R^8$ and $R^{10}$ taken together form a $C_2$-$C_4$ alkylene group, and $R^9$ represents a hydrogen atom, a $C_1$-$C_6$ alkyl group, or a $C_1$-$C_6$ alkoxy group; at least one of $R^2$ and $R^6$ is a halogen atom and the other is a hydrogen atom or a halogen atom; and $R^3$, $R^4$, $R^5$, and $R^7$ are the same or different and are each a hydrogen atom, a $C_{1-6}$ alkyl group, or a halogen atom.

Preferably, in formula (1B), $X^1$ and $X^2$ are the same or different and are each a fluoro $C_1$-$C_4$ alkyl group or a halogen atom; $R^{1a}$ is a hydrogen atom or a $C_1$-$C_4$ alkyl group; at least one of $R^2$ and $R^6$ is a halogen atom and the other is a hydrogen atom or a halogen atom; and $R^3$, $R^4$, $R^5$, and $R^7$ are the same or different and each represent a hydrogen atom, a $C_1$-$C_6$ alkyl group, or a halogen atom.

When the present compound (1) has an asymmetric carbon atom, an enantiomer may be present and the enantiomer and a racemate are both included in the present invention.

The present compound (1) may be produced in accordance with, for example, the following reaction scheme.

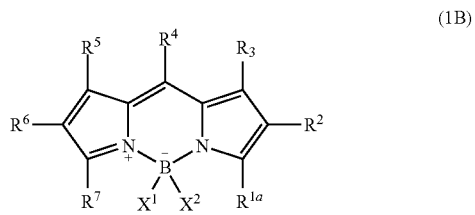

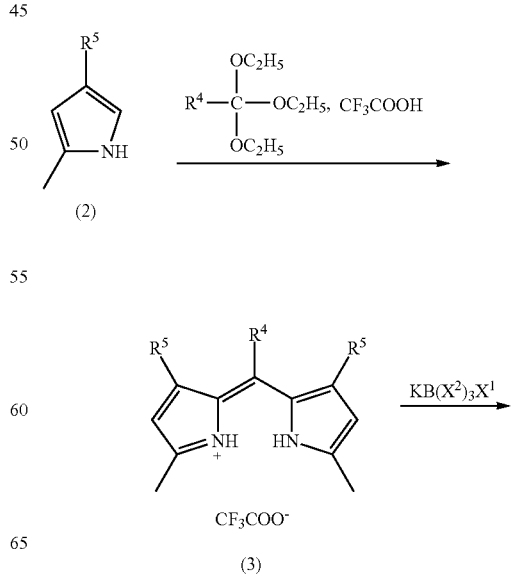

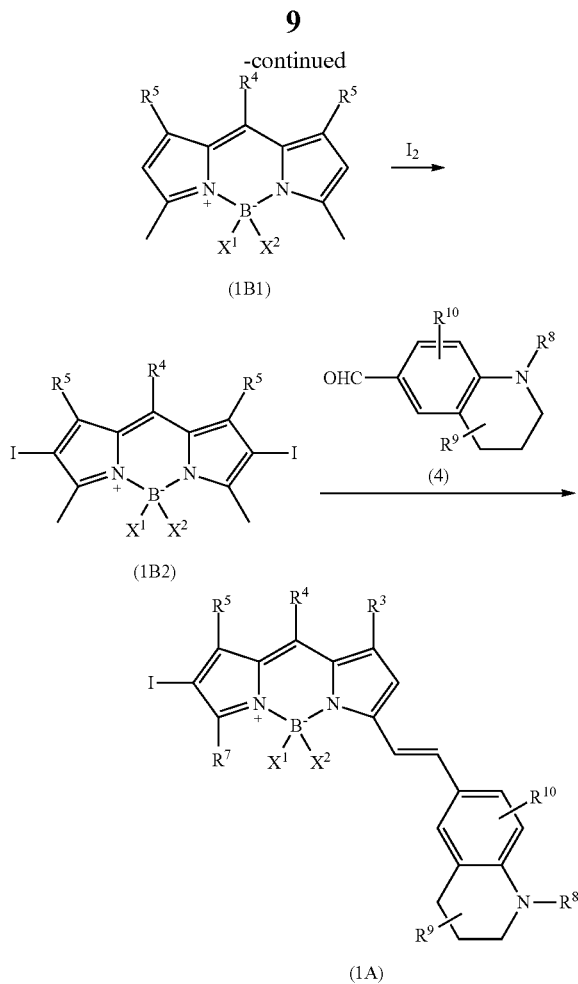

(In the scheme, $X^1$, $X^2$, $R^4$, $R^5$, $R^8$, $R^9$, and $R^{10}$ are the same as above.)

First, a pyrrole compound (2) is reacted with a triethyl orthoformate compound in the presence of an acid such as trifluoroacetic acid to give a compound (3). For example, acetic acid other than trifluoroacetic acid may be used as the acid. This reaction may be performed in an inert solvent such as dichloromethane, chloroform, or dichloroethane at 0 to 50° C. for 10 min to 10 hours.

Next, the compound (3) is reacted with a halogenoalkyl-modified trihalogenoboron (e.g., $KBF_3CF_3$, $KBF_3C_2F_5$) to give a compound (1B1). In this reaction, the compound (3) is first reacted with an organic amine such as triethylamine in a solvent such as dichloromethane. The resultant was reacted at 0° C. with, for example, an acetonitrile suspension containing a halogenoalkyl-modified trihalogenoboron and a Lewis acid such as trimethylsilyl trifluoromethanesulfonic acid (TMSOTf). After that, the reaction may be conducted at 0° C. to room temperature for 1 to 10 hours.

Then, the compound (1B1) is reacted with a halogen such as iodine to give a compound (1B2). The iodination is preferably performed using an iodination agent such as diacetoxy iodobenzene and iodine. Note that the reaction may be conducted in a polar solvent such as acetonitrile at room temperature for 1 to 10 hours.

After that, (1B2) is reacted with a compound (4) to give a compound (1A). This reaction may be carried out in the presence of an acid such as acetic acid and an organic amine such as piperidine in an inert solvent such as toluene at 100 to 200° C. for 1 to 10 hours. In this reaction, an iodine atom is considered to detach from the boron-dipyrrin ring of the compound (1B2).

Note that the compound (4) may be produced, for example, by performing a Vilsmeier-Haack reaction where a tetrahydroquinoline compound is reacted with dimethylformamide and phosphoryl trichloride to formylate the tetrahydroquinoline compound at position 6.

Regarding a substituent on the dipyrrin structure, various kinds of the substituent of a starting material pyrrole compound may be used for appropriate substitution.

In addition, the compound (1A) wherein $R^8$ is $—(CH_2)_l—CONH—(CH_2)_m—Z$ may be obtained by the reaction using $H_2N(CH_2)_n—Z$ and, as a starting material, the compound (4) wherein $R^8$ is $—(CH_2)_l—COOH$.

The present compound (1) as so obtained may be isolated and purified from a reaction mixture by using conventional techniques such as washing, crystallization, recrystallization, and chromatography.

The maximum light absorption wavelength of the present compound (1A) is shifted to the long-wavelength side when compared to that of thioflavin T. It was observed that regarding the present compound (1A) placed in the presence of Aβ, the light absorption wavelength was shifted a little more to the long-wavelength side than in the absence of Aβ and the compound exhibited remarkably high fluorescence. These results demonstrate that like thioflavin T, the present compound is bound to Aβ to inhibit an intramolecular rotation, which results in fluorescence emission.

In addition, when the present compound (1A) was added to native Aβ and was irradiated with light with a wavelength of 590 nm or more under physiological conditions, the amount of native Aβ decreased over time so as to increase the amount of oxygenated Aβ to which one to four oxygen atoms were added. The oxygenation efficiency was remarkably higher than that of thioflavin T. Also, the oxygenation reaction catalyzed by the present compound (1A) is selective for Aβ such that its selectivity is very weak with respect to non-amyloid peptides (e.g., angiotensin IV, methionine enkephalin).

Further, the present compound (1A) had higher oxygenation activity on very toxic aggregated peptides than toward Aβ peptide monomers. Furthermore, the present compound (1A) has superior stability to water and stability under light irradiation conditions.

Hence, the present compound (1A) should work as a catalyst which helps selectively oxygenate pathogenic amyloids such as Aβ peptide, amylin, transthyretin, α-synuclein, tau protein, and huntingtin. Once oxygenated, such a pathogenic amyloid cannot form a stacked β-sheet structure, so that its pathogenicity does not occur. Thus, the present compound (1A) is useful as a drug for preventing and/or treating diseases involving a pathogenic amyloid, such as Alzheimer's disease, Parkinson's disease, diabetes mellitus, Huntington's disease, and systemic amyloidosis in animal including a human.

The present compound (1A) catalyzes a reaction in which a pathogenic amyloid is oxygenated. This oxygenation reaction proceeds such that the present compound (1A) is excited by light exposure and is thus activated to oxygenate amyloid. Because of this, when the present compound (1A) is used as a medicament, a patient is preferably irradiated with light after the present compound (1A) is administered. In addition, the light wavelength which enables the present compound (1A) to be under an excited state is a long-wavelength of 590 run or more. Light with this characteristic wavelength is easy to permeate through a living body.

Meanwhile, examples of the amino acid residue in the amyloid that is oxygenated due to the action of the present compound (1A) include a methionine residue having a sulfur atom and a histidine residue having an imidazole ring.

A pharmaceutical composition comprising the present compound (1A) may be prepared, in accordance with a variety of formulation preparation processes, by selecting an appropriate formulation depending on an administration method and by using a pharmaceutically acceptable carrier. Examples of a dosage form of the pharmaceutical composition comprising, as a main ingredient, the present compound (1A) can include oral preparations such as a tablet, a powder, a granule, a capsule, a liquid, a syrup, an elixir, and an oily or aqueous suspension).

An injection may contain a stabilizer, a preservative, and/or a dissolution aid in a preparation. A solution which may contain such pharmaceutical aids may be placed in a container and provided, for example, as a lyophilized solid preparation, which will be prepared upon use. In addition, a single dose may be contained in a container. Also, multiple doses may be contained in a container.

Meanwhile, examples of an external preparation thereof include a liquid, a suspension, an emulsion, an ointment, a gel, a cream, a lotion, a spray, and a patch.

A solid preparation may contain the present compound (1A) and a pharmaceutically acceptable additive. Examples of the additive include fillers, thickeners, binders, disintegrants, solubilization enhancers, wetting agents, and lubricants. These additives may be selected, as needed, and mixed for formulation.

Examples of a liquid preparation thereof include a solution, a suspension, and an emulsion. The liquid preparation may contain, as an additive, a suspending agent and/or an emulsifying agent.

The present compound (1A) may be used as a human medicament. In this case, an adult daily dose ranges from 1 mg to 1 g and preferably from 1 mg to 300 mg.

EXAMPLES

The following specifically describes the present invention by referring to Examples. The scope of the present invention, however, is not limited to these Examples.

Synthesis Examples

The following experiments were all carried out using a dehydrated solvent under an argon atmosphere.

Synthesis Example 1

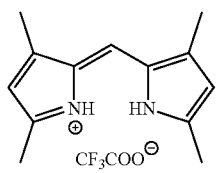

(Compound 1)

First, trifluoroacetic acid (1.2 mL, 15.75 mmol) was added dropwise to a dichloromethane solution (35 mL) containing 2,4-dimethyl pyrrole (2.16 mL, 21 mmol) and triethyl orthoformate (1.75 mL, 10.5 mmol). Next, the mixture was stirred at room temperature for 2 hours. Then, the reaction solution was diluted with water and was extracted using dichloromethane to recover an organic layer. The organic layer was washed with saturated saline and dried over anhydrous sodium sulfate. After the organic solvent was removed under reduced pressure, the remainder was dissolved in a small amount of dichloromethane. Subsequently, hexane was added to the resulting solution to yield precipitates. The precipitates were filtered and washed with hexane to give compound 1 as an orange solid (2.73 g, 83%).

$^1$H NMR (CDCl$_3$, 400 MHz): δ 2.32 (s, 6H), 2.49 (s, 6H), 6.14 (s, 2H), 7.05 (s, 1H); $^{13}$C NMR (CDCl$_3$, 100 MHz): δ 12.08, 14.23, 117.41, 118.18, 120.13, 146.30, 155.30, 161.39; $^{19}$F NMR (CDCl$_3$, 370 MHz): δ −78.10

Synthesis Example 2

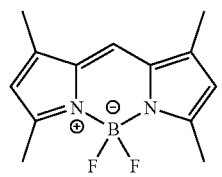

(Compound 2)

First, triethylamine (266 µL, 1.91 mmol) was added to a dichloromethane solution (3 mL) containing compound 1 (100 mg, 0.32 mmol). Next, the mixture was stirred at room temperature for 10 min. To the reaction solution was added dropwise a boron trifluoride-diethyl ether complex (353 mL, 2.86 mmol). The mixture was further stirred at room temperature for 1 hour. Then, the reaction solution was diluted with water and was extracted using dichloromethane to recover an organic layer. The organic layer was washed with saturated saline and dried over anhydrous sodium sulfate. After the organic solvent was removed under reduced pressure, the remainder was purified by flash column chromatography (using an eluent ratio of hexane:ethyl acetate=15:1) to give compound 2 as a red solid (70 mg, 89%).

$^1$H NMR (CDCl$_3$, 400 MHz): δ 2.22 (s, 6H), 2.51 (s, 6H), 6.02 (s, 2H), 7.01 (s, 1H); $^{13}$C NMR (CDCl$_3$, 100 MHz): δ 11.24, 14.63, 118.96, 120.04, 133.38, 141.17, 156.69; $^{19}$F NMR (CDCl$_3$, 370 MHz): δ −149.41

Synthesis Example 3

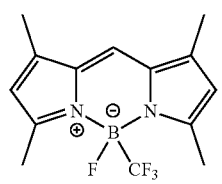

(Compound 3)

First, an aqueous ammonia solution (28% in water, 1.16 mL, 17.2 mmol) was added to a diethyl ether suspension (150 mL) containing compound 1 (1.35 g, 4.3 mmol). Next, the mixture was stirred at room temperature for 20 min. Then, the reaction solution was diluted with water and was extracted using diethyl ether. An organic layer was dried over anhydrous sodium sulfate and the solvent was removed under reduced pressure to give a solid.

After that, trimethylsilyl trifluoromethanesulfonate (6.2 mL, 34.5 mmol) was added dropwise to an acetonitrile suspension (30 mL) containing ice-cold trifluoro(trifluoromethyl)potassium borate (3.03 g, 4.3 mmol) at 0° C. Next, the mixture was stirred at 0° C. for 20 min. To this reaction solution stirred at 0° C. was added dropwise a solution containing N,N-diisopropylethylamine (2.25 mL, 12.9 mmol) and the above solid which had been stirred at room temperature for 10 min in dichloromethane (110 mL). Subsequently, the temperature of the mixture was raised to room temperature and the mixture was then stirred for 3 hours. After an organic solvent was removed under reduced pressure, the remainder was extracted using dichloromethane to recover an organic layer. The organic layer was washed with water and saturated saline and dried over anhydrous sodium sulfate. After the organic solvent was removed under reduced pressure, the remainder was purified by flash column chromatography (using an eluent ratio of hexane:ethyl acetate=15:1) to give compound 3 as a red solid (737 mg, 58%).

$^1$H NMR (CDCl$_3$, 400 MHz): δ 2.25 (s, 6H), 2.51 (s, 6H), 6.08 (s, 2H), 7.08 (s, 1H); $^{13}$C NMR (CDCl$_3$, 100 MHz): δ 11.31, 14.96 (m), 119.76, 120.84, 133.14, 141.71, 157.92; $^{19}$F NMR (CDCl$_3$, 370 MHz): δ −185.83 (1F), −76.46 (3F); LRMS (DART): m/z calcd. for C$_{14}$H$_{16}$BF$_4$N$_2^+$ [M+H]$^{3⊕}$: 299.1, found: 299.2.

Synthesis Example 4

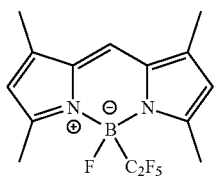

(Compound 4)

Except that trifluoro(pentafluoroethyl)potassium borate was used, the same procedure as in (compound 3) was repeated to give compound 4 as a red solid (the yield: 23%).

$^1$H NMR (CDCl$_3$, 400 MHz): δ 2.25 (s, 6H), 2.51 (s, 6H), 6.07 (s, 2H), 7.07 (s, 1H); $^{13}$C NMR (CDCl$_3$, 100 MHz): δ 11.31, 15.08 (m), 119.77, 133.29, 141.81, 158.34; $^{19}$F NMR (CDCl$_3$, 370 MHz): δ −185.18 (1F), −133.76 (2F), −86.44 (3F); LRMS (DART): m/z calcd. for C$_{15}$H$_{16}$BF$_6$N$_2^+$ [M+H]$^+$: 349.1, found: 349.2.

Synthesis Example 5

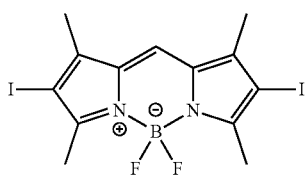

(Compound 5)

To an acetonitrile solution (50 ml) containing compound 2 (100 mg, 0.4 mmol) were added iodine (113 mg, 0.44 mmol) and iodobenzene diacetate (143 mg, 0.44 mmol). Next, the mixture was stirred at room temperature for 3 hours. The reaction solution was diluted with a sodium thiosulfate aqueous solution and was then extracted using ethyl acetate to recover an organic layer. The organic layer was washed with water and saturated saline and dried over anhydrous sodium sulfate. After the organic solvent was removed under reduced pressure, the remainder was purified by flash column chromatography (using an eluent ratio of hexane:ethyl acetate=10:1) to give compound 5 as a red solid (167 mg, 84%).

$^1$H NMR (CDCl$_3$, 400 MHz): δ 2.18 (s, 6H), 2.57 (s, 6H), 7.06 (s, 1H); $^{13}$C NMR (CDCl$_3$, 100 MHz); δ 13.73, 15.65, 81.99, 120.22, 132.80, 144.34, 157.67; $^{19}$F NMR (CDCl$_3$, 370 MHz): δ −148.82. LRMS (ESI-) (m/z) 498.9 [M−1]$^{-1}$ (calc: 498.9).

Synthesis Example 6

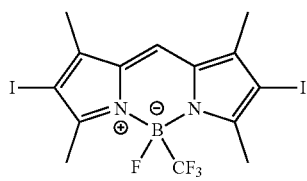

(Compound 6)

Except that compound 3 was used, the same procedure as in Synthesis Example 5 was repeated to give compound 6 as a red solid (the yield: 91%).

$^1$H NMR (CDCl$_3$, 400 MHz): δ 2.24 (s, 6H), 2.58 (s, 6H), 7.16 (s, 1H); $^{19}$F NMR (CDCl$_3$, 370 MHz): δ −183.8 (s, 1F), −76.6 (s, 3F). LRMS (ESI-) (m/z) 548.9 [M−1]$^{-1}$ (calc: 548.9).

Synthesis Example 7

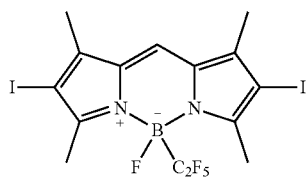

(Compound 7)

Except that compound 4 was used, the same procedure as in Synthesis Example 5 was repeated to give compound 7 (the yield: 77%).

$^1$H NMR (CDCl$_3$, 400 MHz): δ 2.19 (s, 6H), 2.52 (s, 6H), 7.10 (s, 1H); $^{19}$F NMR (CDCl$_3$, 370 MHz): δ −215.37 (1F), −166.09 (2F), −118.33 (3F); LRMS (ESI): m/z calcd for C$_{15}$H$_{12}$BF$_6$I$_2$N$_2^-$ [M−H]$^{-1}$; 598.9, found: 599.0.

Synthesis Example 8

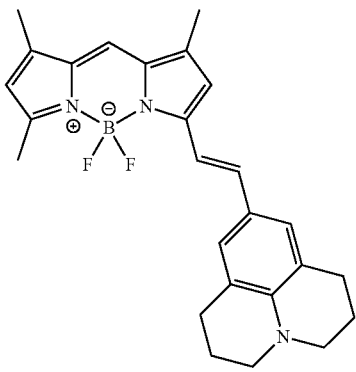
(Compound 8)

First, piperidine (99 μL, 1 mmol) was added to a toluene solution (3 mL) containing compound 2 (25 mg, 0.1 mmol) and 9-julolidine carboxaldehyde (24 mg, 0.12 mmol). Next, the mixture was heated under reflux for 2 hours by using a Dean-Stark apparatus. Then, the reaction solution was cooled to room temperature. After the toluene was removed under reduced pressure, the remainder was purified by flash column chromatography (using an eluent ratio of hexane:ethyl acetate=7:1) to give compound 8 as a blue solid (18 mg, 26%).

$^1$H NMR (CDCl$_3$, 400 MHz): δ 1.94 (m, 4H), 2.22 (s, 3H), 2.25 (s, 3H), 2.54 (s, 3H), 2.74 (t, J=6.27 Hz, 4H), 3.21 (t, J=5.41 Hz, 4H), 5.99 (s, 1H), 6.62 (s, 1H), 6.89 (s, 1H), 7.04 (s, 2H), 7.13 (d, J=15.7 Hz, 1H), 7.31 (d, J=15.7 Hz, 1H); $^{19}$F NMR (CDCl$_3$, 370 MHz): δ −145.86. LRMS (ESI+) (m/z) 431.8 (M$^+$) (calc: 432.2).

Synthesis Example 9

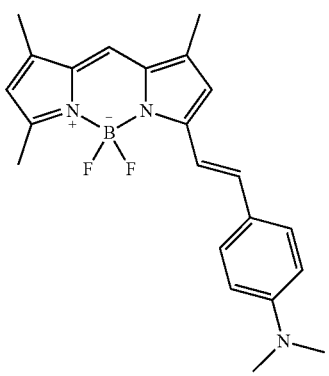
(Compound 9)

Except that compound 2 and 4-(dimethylamino)benzaldehyde were used, the same procedure as in Synthesis Example 8 was repeated to give compound 9 (the yield: 51%).

$^1$H NMR (CDCl$_3$, 400 MHz): δ 2.23 (s, 3H), 2.26 (s, 3H), 2.54 (s, 3H), 3.01 (s, 6H), 6.01 (s, 1H), 6.64-6.67 (br, 3H), 6.93 (s, 1H), 7.21 (d, J=16.1 Hz, 1H), 7.40 (d, J=16.1 Hz, 1H), 7.48 (d, J=8.97 Hz); 19F NMR (CDCl$_3$, 370 MHz): δ −142.83; LRMS (ESI): m/z calcd for C$_{22}$H$_{25}$BF$_2$N$_3^+$ [M+H]$^+$: 380.2, found: 380.1.

Synthesis Example 10

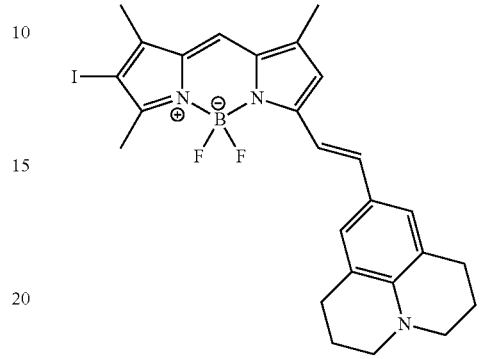
(Compound 10)

Except that compound 5 was used, the same procedure as in Synthesis Example 8 was repeated to give compound 10 as a blue solid (the yield: 19%).

$^1$H NMR (CDCl$_3$, 400 MHz): δ 1.94 (m, 4H), 2.22 (s, 3H), 2.25 (s, 3H), 2.54 (s, 3H), 2.74 (s, 4H, broad), 3.21 (s, 4H, broad), 5.99 (s, 1H), 6.62 (s, 1H), 6.89 (s, 1H), 7.04 (s, 2H), 7.13 (d, J=16.1 Hz, 1H), 7.30 (d, J=16.1 Hz, 1H); $^{19}$F NMR (CDCl$_3$, 370 MHz): δ −145.95.

Synthesis Example 11

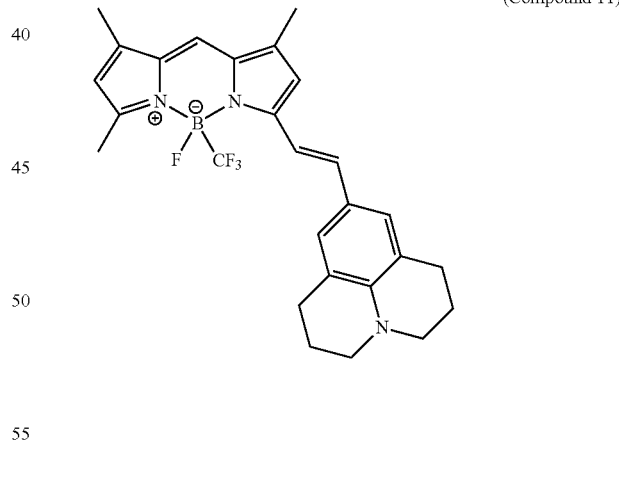
(Compound 11)

The same procedure as in Synthesis Example 8 was repeated to produce, from compound 3, compound 11 as a blue solid (the yield: 40%).

$^1$H NMR (CDCl$_3$, 400 MHz): δ 1.94 (m, 4H), 2.24 (s, 3H), 2.27 (s, 3H), 2.53 (s, 3H), 2.74 (t, J=6.27 Hz, 4H), 3.21 (t, J=5.41 Hz, 4H), 6.04 (s, 1H), 6.69 (s, 1H), 6.94 (s, 1H), 7.15 (d, J=15.7 Hz, 1H), 7.35 (d, J=15.7 Hz, 1H); $^{19}$F NMR (CDCl$_3$, 370 MHz): δ −182.48 (s, 1H), −76.32 (s, 3H). LRMS (ESI+) (m/z) 481.8 (M$^+$) (calc: 482.2).

Synthesis Example 12

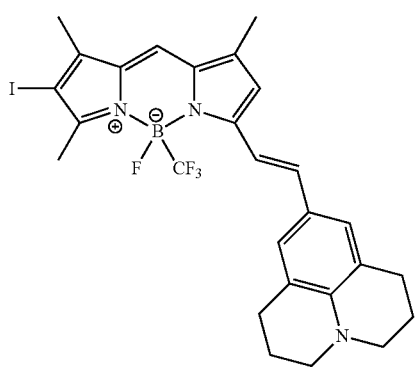
(Compound 12)

The same procedure as in Synthesis Example 8 was repeated to produce, from compound 5, compound 12 as a blue solid (the yield: 43%).

$^1$H NMR (CDCl$_3$, 400 MHz): δ 1.9451 (m, 4H), 2.21 (s, 3H), 2.27 (s, 3H), 2.58 (s, 3H), 2.74 (t, J=5.80 Hz, 4H), 3.23 (t, J=5.83 Hz, 4H), 6.74 (s, 1H), 6.93 (s, 1H), 7.03 (s, 2H), 7.22 (d, J=15.7 Hz, 1H), 7.36 (d, J=15.7 Hz, 1H); $^{19}$F NMR (CDCl$_3$, 370 MHz): δ −181.43 (s, 1H), −76.34 (s, 3H).

Synthesis Example 13

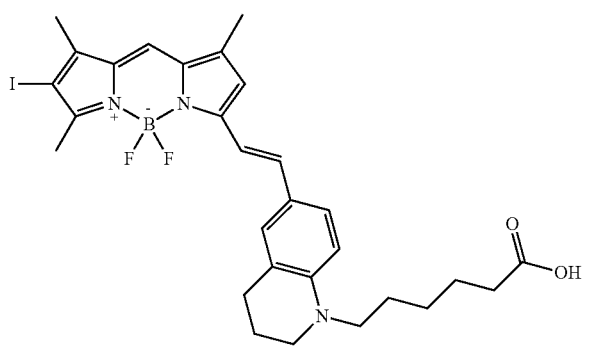
(Compound 13)

Except that compound 5 and 6-formyl-1,2,3,4-tetrahydroquinoline-hexanoic acid were used, the same synthesis procedure as in Synthesis Example 8 was repeated to give compound 13 (the yield: 39%).

$^1$H NMR (acetone-d$_6$, 400 MHz): δ 1.31 (m, 2H), 1.50-1.57 (m, 4H), 1.82 (m, 2H), 2.10 (s, 3H), 2.16-2.21 (m, 5H), 2.40 (s, 3H), 2.66 (t, J=6.27, 2H), 3.25-3.32 (m, 4H), 6.56 (d, J=8.50, 1H), 6.83 (s, 1H), 7.12 (s, 1H), 7.18-7.22 (m, 2H), 7.29 (s, 1H), 7.40 (d, J=16.1 Hz, 1H); $^{19}$F NMR (acetone-d$_6$, 370 MHz): δ −177.2; LRMS (ESI): m/z calcd for C$_{29}$H$_{34}$BF$_2$IN$_3$O$_2$$^+$ [M+H]$^+$: 632.2, found: 632.2.

Synthesis Example 14

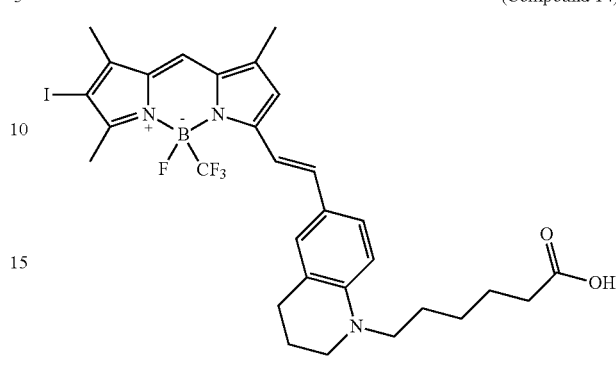
(Compound 14)

Except that compound 6 and 6-formyl-1,2,3,4-tetrahydroquinoline-hexanoic acid were used, the same synthesis procedure as in Synthesis Example 8 was repeated to give compound 14 (the yield: 23%).

$^1$H NMR (acetone-d$_6$, 400 MHz): δ 1.30 (m, 2H), 1.47-1.58 (m, 4H), 1.81 (m, 2H), 2.12 (s, 3H), 2.17-2.22 (m, 5H), 2.43 (s, 3H), 2.65 (t, J=6.28 Hz, 2H), 3.25-3.32 (m, 4H), 6.56 (d, J=8.54, 1H), 6.93 (s, 1H), 7.10 (s, 1H), 7.19-7.27 (m, 2H), 7.37 (s, 1H), 7.43 (d, J=15.7 Hz, 1H); $^{19}$F NMR (acetone-d$_6$, 370 MHz): δ −178a.6 (1F), −73.67 (3F); LRMS (ESI): m/z calcd for C$_{30}$H$_{34}$BF$_4$IN$_3$O$_2$$^+$ [M+H]$^+$: 682.2, found: 682.5.

Synthesis Example 15

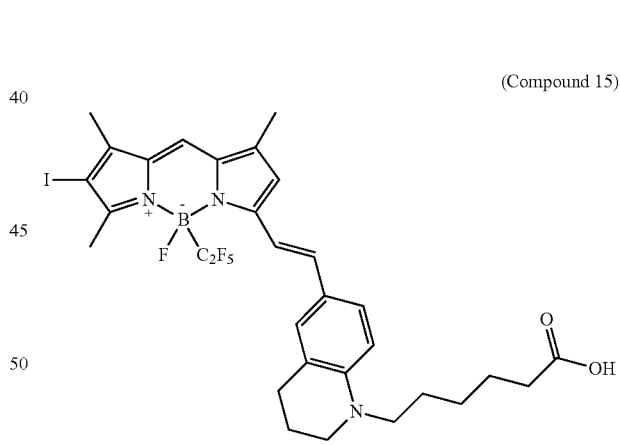
(Compound 15)

Except that compound 7 and 6-formyl-1,2,3,4-tetrahydroquinoline-hexanoic acid were used, the same synthesis procedure as in Synthesis Example 8 was repeated to give compound 15 (the yield: 13%).

$^1$H NMR (acetone-d$_6$, 400 MHz): δ 1.31 (m, 2H), 1.50-1.57 (m, 4H), 1.82 (m, 2H), 2.12 (s, 3H), 2.15-2.22 (m, 5H), 2.43 (s, 3H), 2.65 (t, J=6.28, 2H), 3.25-3.32 (m, 4H), 6.57 (d, J=8.54, 1H), 6.93 (s, 1H), 7.10 (s, 1H), 7.20 (d, J=8.54, 1H), 7.28 (d, J=15.7 Hz, 1H), 7.37 (s, 1H), 7.43 (d, J=15.7 Hz, 1H); $^{19}$F NMR (acetone-d$_6$, 370 MHz): δ −177.9 (1F), −131.2 (2F), −84.03 (3F); LRMS (ESI): m/z calcd for C$_{31}$H$_{34}$BF$_6$IN$_3$O$_2$$^+$ [M+H]$^+$: 732.2, found: 731.1.

Synthesis Example 16

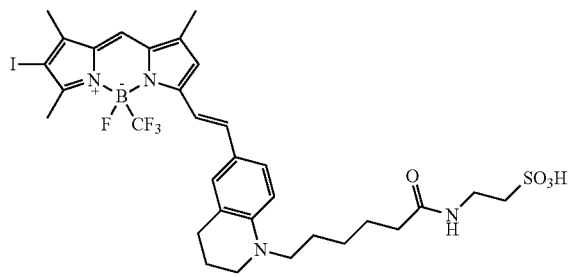

(Compound 16)

To DMF (2 mL) in which compound 15 (10.5 mg, 0.015 mmol) and taurine (40 mg, 0.32 mmol) had been dissolved were added 1-ethyl-3-(3-dimethylamino)propyl)carbodiimide (EDC) (15 mg, 0.078 mmol), N,N-diisopropylethylamine (DIPEA) (13 μL, 0.075 mmol), and 1-hydroxybenzotriazole (HOBt.H$_2$O) (10.5 mg, 0.078 mmol). Next, the reaction mixture was stirred overnight at room temperature. The reaction mixture was purified by HPLC to give compound 16 as a dark blue solid.

The yield (2.1 mg, 17%). LRMS (ESI): m/z calcd for C$_{32}$H$_{39}$BF$_4$IN$_4$O$_4$S$^+$ [M+H]$^+$: 789.2, found: 789.4; HPLC: t$_R$=36.8 min (based on HPLC analysis at 230 nm with a linear gradient of 0-100% MeCN in 0.1% aq. TFA over 40 min).

Reference Example 1 (Synthesis of 6-formyl-1,2,3,4-tetrahydroquinoline-hexanoic acid)

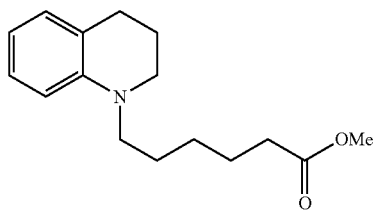

(1)

To an acetonitrile suspension (10 mL) containing sodium iodide (6.4 g, 38.2 mmol) and sodium carbonate (4.4 g, 31.8 mmol) were added 1,2,3,4-tetrahydroquinoline (2.0 mL, 15.9 mmol) and methyl 6-bromohexanoate (3.0 mL, 19.1 mmol). The reaction solution was heated under reflux for 48 hours. Next, the reaction solution was cooled to room temperature. Subsequently, the reaction mixture was filtered and the organic solvent was removed under reduced pressure. The remainder was diluted with water and then extracted using ethyl acetate. The organic layer was washed with saturated saline and dried over anhydrous sodium sulfate. After the organic solvent was removed under reduced pressure, the remainder was purified by silica gel column chromatography (using an eluent ratio of hexane:ethyl acetate=10:1) to give 1,2,3,4-tetrahydroquinoline-methyl hexanoate as a pale yellow oily substance (3.36 g, 81%).

$^1$H NMR (CDCl$_3$, 400 MHz): δ 1.37 (m, 2H), 1.57-1.74 (m, 4H), 1.94 (m, 2H), 2.33 (t, J=7.48, 2H), 2.75 (t, J=6.74, 2H), 3.17-3.28 (m, 4H), 3.67 (s, 3H), 6.53-6.56 (m, 2H), 6.93 (d, J=5.96, 1H), 7.04 (t, J=7.48, 1H); LRMS (ESI): m/z calcd for C$_{16}$H$_{24}$NO$_2$$^+$ [M+H]$^+$: 262.2, found: 262.2.

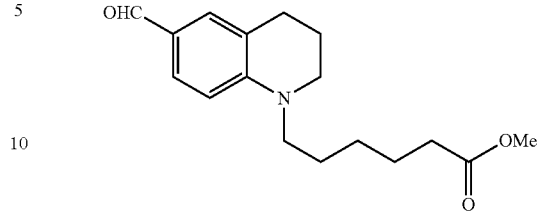

(2)

To dichloromethane (15 mL) in which 1,2,3,4-tetrahydroquinoline-methyl hexanoate (2.25 g, 8.6 mmol) had been dissolved was added phosphoryl chloride (2.4 mL, 25.8 mmol) at 0° C. Next, DMF (6.7 mL, 86 mmol) was added slowly dropwise thereto at 0° C. Then, the temperature of the reaction mixture was raised to room temperature and the reaction mixture was stirred for 2 hours.

Subsequently, the reaction mixture was diluted with water, and aqueous sodium hydroxide at 0° C. was added thereto to bring the pH to 7. After the solvent was removed under reduced pressure, the remainder was extracted using ethyl acetate. The organic layer was washed with saturated saline and dried over anhydrous sodium sulfate. After the organic solvent was removed under reduced pressure, the remainder was purified by silica gel column chromatography (using an eluent ratio of hexane:ethyl acetate=3:1) to give 6-formyl-1,2,3,4-tetrahydroquinoline-methyl hexanoate as a pale yellow oily substance (1.8 g, 73%).

$^1$H NMR (CDCl$_3$, 400 MHz): δ 1.36 (m, 2H), 1.56-1.69 (m, 4H), 1.90 (m, 2H), 2.30 (t, J=7.48, 2H), 2.73 (t, J=5.97, 2H), 3.27-3.35 (m, 4H), 3.63 (s, 3H), 6.51 (d, J=8.97, 1H), 7.41 (s, 1H), 7.49 (dd, J=1.92, 8.60 Hz, 1H), 9.60 (s, 1H); LRMS (ESI): m/z calcd for C$_{17}$H$_{24}$NO$_3$$^+$ [M+H]$^+$: 290.2, found: 290.1.

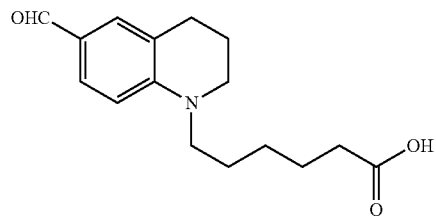

(3)

To methanol (10 mL) in which 6-formyl-1,2,3,4-tetrahydroquinoline-methyl hexanoate (1.08 g) had been dissolved was added 5 N potassium hydroxide (6 mL). Next, the mixture was stirred at room temperature for 5 hours. After the solvent was removed under pressure from the reaction mixture, the remainder was diluted with water and washed with ethyl acetate. An aqueous hydrochloric acid solution was added to an aqueous layer to bring the pH to 1. Subsequently, the mixture was extracted using ethyl acetate and the extract was dried over anhydrous sodium sulfate. After the organic solvent was removed under reduced pressure, the remainder was purified by silica gel column chromatography (using an eluent ratio of dichloromethane:methanol=10:1; 1% AcOH was included) to give 6-formyl-1,2,3,4-tetrahydroquinoline-hexanoic acid as a brown solid (914 mg, 89%).

$^1$H NMR (CDCl$_3$, 400 MHz): δ 1.39 (m, 2H), 1.59-1.70 (m, 4H), 1.92 (m, 2H), 2.37 (t, J=7.41 Hz, 2H), 2.75 (t, J=6.29, 2H), 3.29-3.37 (m, 4H), 6.53 (d, J=8.54, 1H), 7.43 (s, 1H), 7.51 (d, J=8.50, 1H), 9.62 (s, 1H); LRMS (ESI): m/z calcd for C$_{16}$H$_{22}$NO$_3$$^+$ [M+H]$^+$: 276.2, found: 276.1.

Reference Example 2 (Synthesis of 1-(2-azido-ethyl)-6-formyl-1,2,3,4-tetrahydroquinoline)

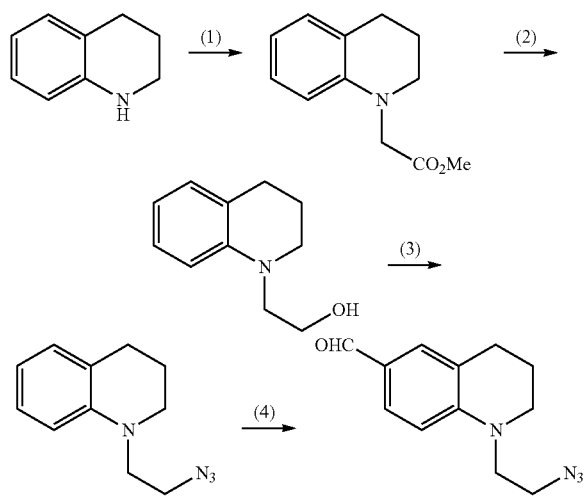

(1) To an acetonitrile suspension (100 mL) containing sodium iodide (31.7 g, 191 mmol) and sodium carbonate (22 g, 160 mmol) were added 1,2,3,4-tetrahydroquinoline (10 mL, 79.6 mmol) and methyl bromoacetate (8.8 mL, 95.5 mmol). Next, the reaction solution was heated under reflux for 6 hours. Next, the reaction solution was cooled to room temperature. Subsequently, the reaction mixture was filtered and the organic solvent was removed under reduced pressure. The remainder was diluted with water and then extracted using ethyl acetate. The organic layer was washed with saturated saline and dried over anhydrous sodium sulfate. Finally, the organic solvent was removed under reduced pressure. Additional purification work was not conducted and the resultant was used in the next reaction.

$^1$H NMR (CDCl$_3$, 500 MHz): δ 1.98 (m, 2H), 2.77 (t, J=6.27 Hz, 2H), 3.38 (t, J=5.72 Hz, 2H), 3.70 (s, 3H), 3.99 (s, 2H), 6.38 (d, J=7.45 Hz, 1H), 6.60 (dd, J=7.45, 7.45 Hz, 1H), 6.95 (d, J=7.45 Hz, 1H), 7.00 (dd, J=7.45, 7.45 Hz, 1H).

(2) Lithium aluminum hydride (3.62 g, 95.5 mmol) was dissolved in tetrahydrofuran (100 mL) and the mixture was cooled to 0° C. To this solution was added over 30 min tetrahydrofuran (400 mL) in which 1,2,3,4-tetrahydroquinoline-methyl ethanoate obtained in the above section (1) had been dissolved. Next, the mixture was stirred at 0° C. for 20 min. Subsequently, the temperature of the mixture was raised to room temperature and the mixture was then stirred for 12 hours. Then, the reaction mixture was cooled to 0° C. Thereafter, water (3.6 mL), 15% aqueous sodium hydroxide (3.6 mL), and water (10.8 mL) were added thereto in this order, and the resulting mixture was further stirred at room temperature for 1 hour. After that, precipitates were removed by celite filtration. After the organic solvent was removed under reduced pressure, the remainder was purified by silica gel column chromatography (using an eluent ratio of hexane:ethyl acetate=1:1) to give a yellow oily substance (12.1 g, 85% over 2 step).

$^1$H NMR (CDCl$_3$, 500 MHz): δ 1.82 (br, 1H), 1.95 (m, 2H), 2.76 (t, J=6.30 Hz, 2H), 3.31 (t, J=5.72 Hz, 2H), 3.42 (t, J=5.72 Hz, 2H), 3.80 (br, 2H), 6.60 (dd, J=6.85, 7.45 Hz, 1H), 6.67 (d, J=8.00 Hz, 1H), 6.95 (d, J=6.85 Hz, 1H), 7.04 (dd, J=7.45, 8.00 Hz, 1H)

(3) To dichloromethane (40 mL) in which 1,2,3,4-tetrahydroquinoline-1-ethanol had been dissolved was added trimethyl amine (1.74 mL, 12.48 mmol). Next, the mixture was stirred at 0° C. for 10 min. Then, methanesulfonyl chloride (725 μL, 9.36 mmol) at 0° C. was added thereto. After the temperature of the reaction mixture was raised to room temperature, the reaction mixture was stirred for 3 hours. Subsequently, the reaction mixture was concentrated under reduced pressure. Then, the concentrate was dissolved in a small amount of ethyl acetate and was subjected to silica gel filtration. The ethyl acetate was removed under reduced pressure to give a yellow oily substance. This oily substance and sodium azide (1.62 g, 25 mmol) were dissolved in DMF (40 mL) and the mixture was then stirred at 60° C. for 1 hour. After that, the reaction solution was diluted with water and was extracted using diethyl ether. The organic layer was washed with saturated saline and dried over anhydrous sodium sulfate. After the organic solvent was removed under reduced pressure, the remainder was purified by silica gel column chromatography (using an eluent ratio of hexane:ethyl acetate=25:1) to give a substance of interest as a colorless oily substance (1128 mg, 89%).

$^1$H NMR (CDCl$_3$, 500 MHz): δ 1.97 (m, 2H), 2.77 (t, J=6.27 Hz, 2H), 3.36 (t, J=5.73 Hz, 2H), 6.58 (d, J=8.00 Hz, 1H), 6.62 (dd, J=7.43, 7.45, 1H), 6.97 (d, J=7.43 Hz), 7.07 (dd, J=7.45, 8.00 Hz, 1H)

(4) To DMF (1.5 mL, 18.4 mmol) was added phosphoryl chloride (572 μL, 6.14 mmol) at 0° C. Next, the temperature of the reaction mixture was raised to room temperature and the reaction mixture was stirred for 1 hour. Then, 1-(2-azidoethyl)-1,2,3,4-tetrahydroquinoline (1128 mg, 5.58 mmol) was added thereto and the reaction was further carried out at 90° C. for 5 hours. After that, the reaction mixture was cooled to 0° C. and diluted with water. Subsequently, a potassium carbonate aqueous solution was added to bring the pH to 7, and the mixture was extracted using diethyl ether. The organic layer was washed with saturated saline and dried over anhydrous sodium sulfate. After the organic solvent was removed under reduced pressure, the remainder was purified by silica gel column chromatography (using an eluent ratio of hexane:ethyl acetate=3:1) to give a substance of interest as a pale yellow oily substance.

$^1$H NMR (CDCl$_3$, 400 MHz): δ 1.95 (m, 2H), 2.77 (t, J=6.28 Hz, 2H), 3.43 (t, J=5.84 Hz, 2H), 3.48-3.56 (m, 4H), 6.58 (d, J=8.63 Hz, 1H), 7.45 (d, J=2.23 Hz, 1H), 7.52 (dd, J=2.23, 8.63 Hz, 1H), 9.65 (s, 1H); LRMS (ESI): m/z calcd for C$_{12}$H$_{15}$N$_4$O$^+$ [M+H]$^+$: 231.1, found: 231.3.

Synthesis Example 17

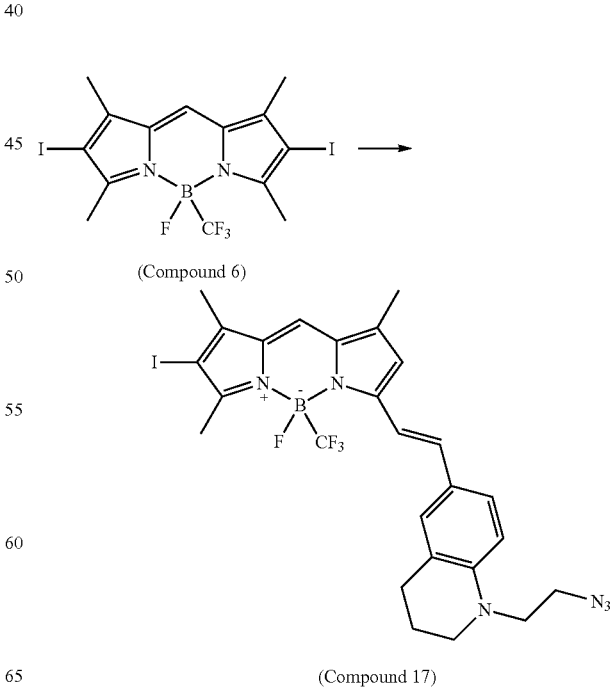

(Compound 6)

(Compound 17)

Except that compound 6 and 1-(2-azidoethyl)-6-formyl-1,2,3,4-tetrahydroquinoline were used, the same synthesis procedure as in Synthesis Example 8 was repeated to give compound 17 (the yield: 29%).

$^1$H NMR (acetone-$d_6$, 500 MHz): δ 1.97 (m, 2H), 2.25 (s, 3H), 2.35 (s, 3H), 2.56 (s, 3H), 3.47-3.66 (m, 8H), 6.78 (d, J=8.57 Hz, 1H), 7.05 (s, 1H), 7.26 (s, 1H), 7.34 (d, J=8.57 Hz, 1H), 7.40 (d, J=16.1 Hz, 1H), 7.53 (s, 1H), 7.56 (d, J=16.1 Hz, 1H)

Synthesis Example 18

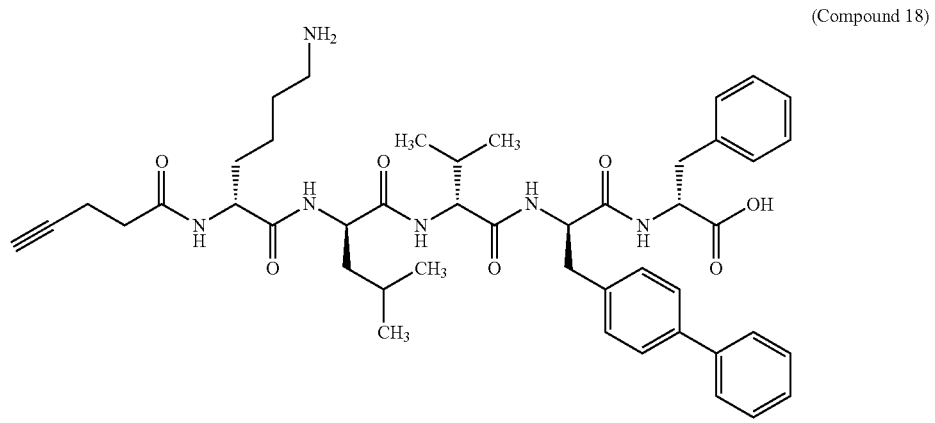 [SMILES: C#CCCC(=O)N[C@H](CCCCN)C(=O)N[C@H](CC(C)C)C(=O)N[C@@H](C(=O)N[C@H](Cc1ccc(-c2ccccc2)cc1)C(=O)N[C@H](Cc1ccccc1)C(=O)O)C(C)C]

(Compound 18)

(1) Target compound 18 was synthesized using Fmoc-protected amino acids and 4-pentynoic acid in accordance with a conventional Fmoc-type peptide solid phase synthesis method.

LRMS (ESI): m/z calcd for $C_{46}H_{61}N_4O_7^+$ [M+H]$^+$: 809.5, found: 809.5; Purity >80% (based on HPLC analysis at 214 nm with a linear gradient of 0-100% MeCN in 0.1% aq. TFA over 40 min).

(2)

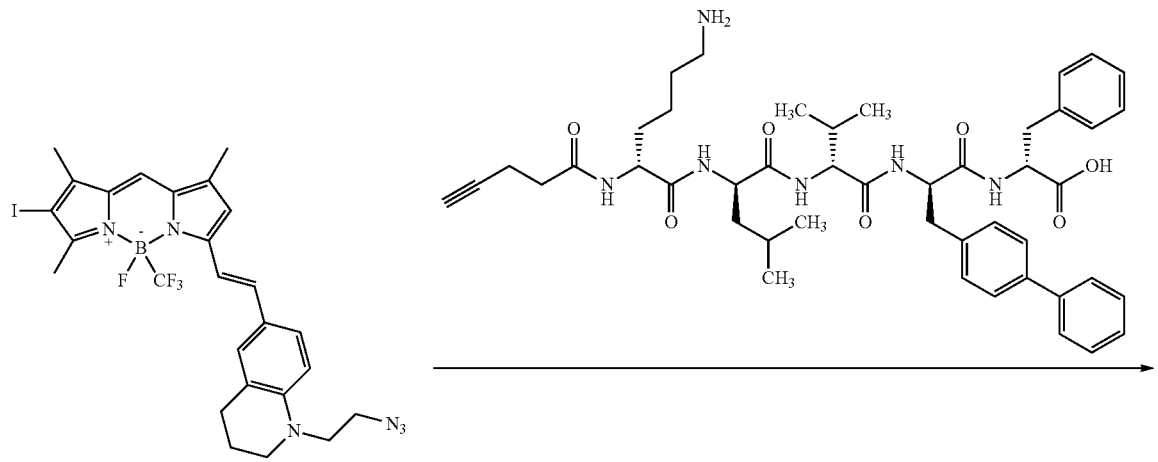

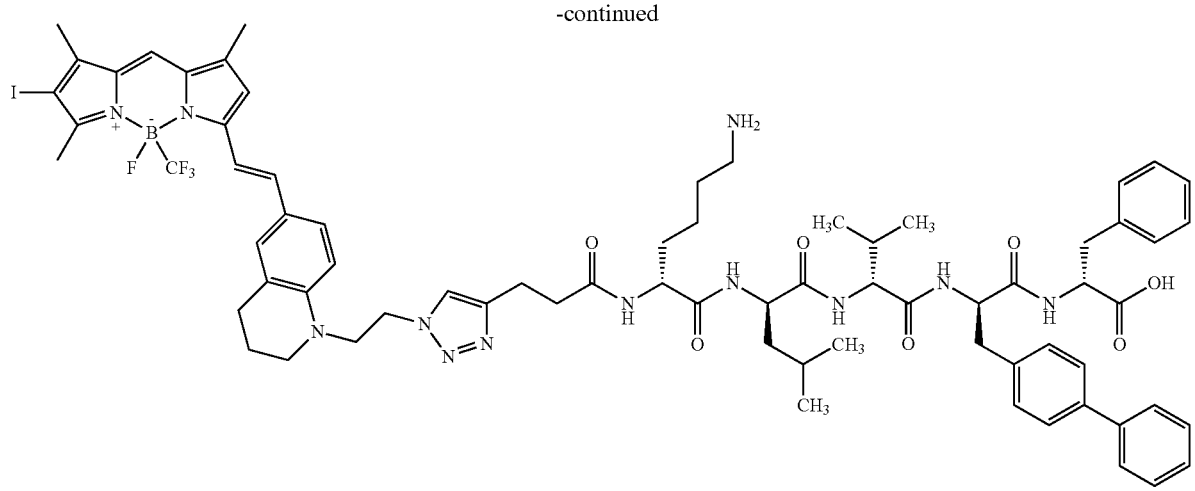

(Compound 19)

According to the disclosure of K. Shinoa, Y. Sohma, M. Kanai, Bioorg. Med. Chem. Lett. 2015, 25, 2976-2979, compound 17 (9.42 mg, 0.0124 mmol) and compound 18 (15 mg, 0.0186 mmol) were dissolved in 1.5 mL of toluene/$^t$BuOH/water (1/1/1). Next, CuSO$_4$.5 H$_2$O (0.31 mg, 10 mol %) and L-ascorbic acid (11 mg, 0.062 mmol) were added thereto, and the mixture was then stirred for 24 hours. After that, the reaction mixture was purified by HPLC to give compound 19 (2.0 mg, 11%).

MALDI-TOF MS: m/z calcd for $C_{72}H_{87}BF_4IN_{12}O_7^+$ [M+H]$^{3O}$: 1445.6, found: 1448.5.

Test Example 1 (Stability to Water)

Phosphate buffer solutions (pH 7.4) in which compound 8, 10, 11, or 12 (each 20 µM) had been dissolved were incubated at 37° C. and the time course of each light absorption spectrum was determined.

The results are shown in FIG. 1. As is clear from FIG. 1, the present compounds in which the boron was substituted with trihalogenoalkyl group had a high stability to water.

Test Example 2 (Optical Properties and Stability Under Light Irradiation Conditions)

The optical properties (in methanol) of compounds 2 to 4 synthesized were determined (Table 1). The compounds 2 to 4 each have maximum absorption at a wavelength at or near 500 nm and emit fluorescence at 509 nm. It was observed that introduction of a perfluoroalkyl group caused some decreases in light absorption coefficients, but little change in their fluorescence quantum yield. This result has demonstrated that the perfluoroalkyl group on the boron atom does not considerably affect the optical properties of the present compounds.

TABLE 1

| Compound | $X^2$ | Absorbance $\lambda_{max}$ (nm) | Emission $\lambda_{max}$ (nm) | $\epsilon$ (M$^{-1}$ cm$^{-1}$) | $\Phi_{fl}$ |
|---|---|---|---|---|---|
| 2 | F | 502 | 509 | 81400 | 0.80 |
| 3 | CF$_3$ | 502 | 509 | 74000 | 0.80 |
| 4 | C$_2$F$_5$ | 503 | 509 | 72600 | 0.79 |

Next, a methanol solution containing each of compounds 2 to 4 was irradiated with light of 500 nm, and incubated at 37° C. Then, a change in the time course of the absorbance at the maximum light absorption wavelength was measured to compare their photostability (FIG. 2). Compound 2 resulted in substantial photofading after about 30 min. By contrast, compounds 3 and 4, having a perfluoroalkyl group, took 2 hours or longer until complete photofading. That is, it was suggested that the present compounds having a perfluoroalkyl group on the boron atom should be more significantly stable against light than the compound having two fluorine atoms on the boron atom. Reaction with singlet oxygen seems to be primarily responsible for the photofading under visible light irradiation. So, the photostability of the present compounds was considered from the viewpoint of the reactivity with singlet oxygen. First, the HOMO/LUMO levels of compounds 2 to 4 were calculated in accordance with a DFT algorithm (FIG. 3). The calculation results demonstrated that the HOMO/LUMO levels decreased in the order of F>CF$_3$>C$_2$F$_5$, which were a substituent on the boron atom. As the HOMO level increases, the compounds are more susceptible to oxygenation by singlet oxygen. Thus, this calculation results agree with the results of the photostability test. In addition, the three compounds exhibited almost no difference with respect to the HOMO-LUMO energy gap. This reflects the fact that the maximum absorption wavelength is unchanged.

Test Example 3

Each absorption spectrum was measured (Table 2). The maximum absorption wavelength of compound 8, in which the dimethylamino phenyl group of compound 9 was changed to a julolidine group, was shifted to the long-wavelength side by 30 nm than that of compound 9. Even when the substituent on the boron atom was changed from F to $CF_3$ (compound 11), there was almost no observable change in the maximum absorption wavelength. The maximum absorption wavelength of compound 12, in which $R^6$ was iodine, was shifted to the long-wavelength side by 20 nm. This allowed the compound to be efficiently excited by light with a longer wavelength of over 650 nm. In the cases of the carboxyl group- or sulfonic acid group-substituted tetrahydroquinoline derivatives (compounds 13 to 16) so as to introduce a water-soluble substituent, the absorption wavelength was shifted to the short-wavelength side by about 10 nm than that of the julolidine-substituted derivative. It can be deduced from the above results that as the lone electron pair of the nitrogen atom is arranged more stably on the same plane as that of the benzene ring due to the condensed ring structure of the julolidine or tetrahydroquinoline, the absorption wavelength tends to be shifted more to the long-wavelength side. Also, it was found that introduction of iodine caused a shift to the long-wavelength side and that the substituent on the boron atom did not significantly affect the absorption wavelength.

TABLE 2

| Compound | $R^6$ | $X^2$ | Absorbance $\lambda_{max}$(nm) |
|---|---|---|---|
| 9 | H | F | 609 |
| 8 | H | F | 639 |
| 11 | H | $CF_3$ | 640 |
| 12 | I | $CF_3$ | 660 |
| 13 | I | F | 647 |
| 14 | I | $CF_3$ | 651 |
| 15 | I | $C_2F_5$ | 651 |
| 16 | I | $CF_3$ | 652 |

Test Example 4

(1) To check whether or not the compounds synthesized actually had Aβ oxygenation activity, in vitro oxygenation experiments were carried out using $Aβ_{1-42}$ as a substrate. Compound 12 (20 μM) was added to a phosphate buffer solution (pH 7.4) containing $Aβ_{1-42}$ (20 μM), and the mixture was incubated at 37° C. under LED light irradiation (at a wavelength of 595 nm). Then, a mass spectrometer (MALDI-TOF MS) was used to follow the reaction. Before the light irradiation, native $Aβ_{1-42}$ and $Na^+$ adducts were primarily observed. After the light irradiation, however, there appeared ion peaks indicating the presence of oxygen adducts in a time-dependent manner (FIG. 4).

(2) The $Aβ_{1-42}$ oxygenation activities of compounds 8, 11, and 12 were compared (FIG. 5). First, 0.1% TFA aqueous solution containing o-acyliso-$Aβ_{1-42}$ was diluted with a phosphate buffer solution (PB) (10 mM, pH 7.4) to prepare a native $Aβ_{1-42}$ solution. To the resulting solution was added a DMSO catalyst stock solution (1.0 M). While incubated at 37° C., the mixture was irradiated with light at 595 nm. The MALDI-TOF MS results demonstrated that compounds 8, 11, and 12 each helped oxygenate $Aβ_{1-42}$ under the light irradiation. The rate of oxygenation of $Aβ_{1-42}$ was significantly faster using compound 12 than compounds 8 and 11 free of a heavy atom such as a bromine atom or an iodine atom. The heavy metal effect seems to enhance the efficiency of generating singlet oxygen. In addition, when comparing the compound 8 and 11, the compound 11 having a boron-trifluoromethyl bond had a faster oxygenation rate than the compounds 8, suggesting that the compound 11 can function as a better Aβ oxygenation catalyst.

(3) Next, the activities of compounds 12, 14, and 16 were compared (FIG. 6). Here, in view of application to multi-component systems such as cells, oxygenation experiments were carried out using DMEM as a solvent. O-acyliso-$Aβ_{1-42}$ was converted to native $Aβ_{1-42}$ in phosphate buffered saline (PBS), followed by incubation at 37° C. for 2 hours to promote aggregation. Then, the resultant was mixed in DMEM. Because the compounds 12, 14, and 16 had a maximum absorption wavelength of more than 650 nm, the reaction was made to proceed by irradiation with light at 660 nm, which was a longer wavelength than that of the preceding experiments. The results demonstrated that the $Aβ_{1-42}$ oxygenation activity of each of the compounds 14 and 16, in which a water-soluble substituent (i.e., a carboxyl group or a sulfonic acid group) was introduced, was significantly larger than that of the compound 12. The oxygenation activity of the compound 16 having a sulfonic acid site was higher than that of the compound 14 having a carboxylic acid site, indicating the tendency that the higher the water solubility, the higher the oxygenation activity. In addition, FIG. 7 shows the $Aβ_{1-42}$ oxygenation activity of compound 19.

(4) To obtain more direct knowledge, compounds 13 to 15 were used to further investigate the functions of an oxygenation photocatalyst having a perfluoroalkyl group on the boron atom. First, the $Aβ_{1-42}$ oxygenation activities of the compounds 13 to 15 were likewise compared (FIG. 8). The results demonstrated that the oxygenation activity was significantly higher in the order of $C_2F_5>CF_3>F$, which were a substituent on the boron atom. This result agrees with the order of the above-described photostability. Accordingly, the level of the catalyst stability is deemed to reflect the activity.

Test Example 5 (Aβ Peptide Selectivity)

Compound 14 was used to investigate whether or not a compound of the present invention was able to selectively oxygenate Aβ. First, compound 14 (20 μM) was added to phosphate buffer solutions (pH 7.4) each containing $Aβ_{1-42}$ (20 μM), angiotensin IV (20 μM) or a methionine enkephalin (20 μM), which solutions had been pre-incubated for 3 hours. The mixtures were incubated at 37° C. for 30 min under LED light irradiation (at a wavelength of 595 nm). Then, a mass spectrometer (MALDI-TOF MS) was used to follow the reaction. Three model peptides having a residue capable of being oxygenated were selected, including angiotensin IV (AT-4), met-enkephalin (ME), and somatostatin (Sat). These three peptides were subjected to the same oxygenation conditions as for $Aβ_{1-42}$ (FIG. 9). In addition, riboflavin was used as a control which exhibited no Aβ selectivity, and the oxygenation experiments were likewise conducted. The results demonstrated that riboflavin exerted a certain oxygenation activity on all the peptides; by contrast, the compound 14 exerted strong oxygenation activity only toward $A\beta_{1-42}$; and the oxygenation of each of the other peptides did not proceed at all or was significantly slower than that of $A\beta_{1-42}$.

Test Example 6 (Oxygenation of Aggregated $A\beta$ Peptides)

In the following, in order to check whether or not compound 14 recognized a cross-$\beta$-sheet structure characteristic of $A\beta$ aggregates to elicit oxygenation activity, dependency of the oxygenation rate on aggregation was examined. An incubation time after o-acyliso-$A\beta_{1-42}$ was converted to native $A\beta_{1-42}$ was used as an index for aggregation process index to check whether or not the oxygenation rate changed depending on the incubation time (FIG. 10). A test compound (each 2 µM) was added to a phosphate buffer solution (pH 7.4) containing $A\beta_{1-42}$ (20 µM), which solution had not been incubated, or phosphate buffer solutions (pH 7.4) each containing $A\beta_{1-42}$ (20 µM), which solutions had been pre-incubated for 1 or 3 hours. The mixtures were incubated at 37° C. for 10 min under LED light irradiation (at a wavelength of 595 nm). Then, a mass spectrometer (MALDI-TOF MS) was used to follow the reaction. The results demonstrated that the longer the incubation time, the faster the oxygenation of $A\beta_{1-42}$. That is, it was found that the richer the cross-$\beta$-sheet structure as a result of aggregation, the faster the oxygenation of $A\beta_{1-42}$. The above has indicated that the compound 14 recognizes the cross-$\beta$-sheet structure to selectively oxygenate aggregated $A\beta$.

Test Example 7 (Test on Cells)

(Method)

$A\beta$ (40 µM) was dissolved in a phosphate buffer solution, and the mixture was incubated at 37° C. for 2 hours. Next, compound 16 was added thereto (at 1.6 µM). Then, 0.1% horse serum-containing Dulbecco's Modified Eagle Medium was added to rat adrenal pheochromocytoma PC12 cells (purchased from RIKEN, Japan) seeded on a poly D-lysine-coated 96-well plate to prepare a mixture. To the mixture was added 25 µL of the above phosphate buffer solution containing $A\beta$ and compound 16 (the final volume: 100 µL; the final $A\beta$ concentration: 10 µM; the final compound 16 concentration: 0.4 µM). After that, this mixed solution was incubated at 37° C. for 5 min under LED light irradiation (at a wavelength of 660 nm; at 10 mW) (provided that in the dark, no light irradiation). The plate containing the cell reaction solution was further incubated at 37° C. for 48 hours under 5% $CO_2$ atmosphere. Finally, a viable-cell count reagent SF containing WST-8 (10 µL; purchased from Nacalai Tesque, Inc.) was added and the resulting mixture was incubated at 37° C. for 3 hours under 5% $CO_2$ atmosphere to measure absorbance at 450 nm (cf., a reference wavelength: 655 nm). From the absorbance, cell viability was determined.

(Results)

Whether or not the oxygenation of $A\beta_{1-42}$ in the presence of cells caused a decrease in cytotoxicity was investigated. Rat adrenal pheochromocytoma model nerve cells PC12 were used as cells and compound 16 with excellent water solubility and oxygenation activity was used as a catalyst to perform a cell viability (FIG. 11). The cell viability was determined by measuring absorbance at 450 nm due to WST-8 using a plate reader. When $A\beta_{1-42}$ and compound 16 were added under no light irradiation, substantially the same level of significant cell death as in the case where only $A\beta_{1-42}$ was added was observed. By contrast, the cell viability under light irradiation significantly increased. That is, it has been demonstrated that the selective oxygenation of $A\beta_{1-42}$ by the catalyst causes a decrease in cytotoxicity.

The present compound represented by formula (1A) has a structure in which an electron donor site and an electron acceptor site rotate around a bond therebetween as a shaft. Even when excited by light in the absence of $A\beta$, the present compound causes no reaction because of the rotation and resultant relaxation. By contrast, when the compound binds to the higher structure of amyloid and the rotation is inhibited, an oxygenation reaction occurs through the production of singlet oxygen. It is considered that since the activity of the present compound is switchable as describe above, the present compound seems can oxygenate $A\beta_{1-42}$ in a highly selectable manner even in a complicated system, for example in the presence of cells.

The invention claimed is:

1. A boron-dipyrrin complex represented by formula (1)

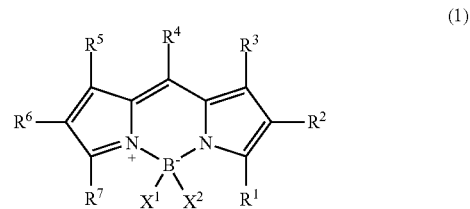

(1)

wherein:

$X^1$ represents a halogenoalkyl group;

$X^2$ represents a halogen atom;

$R^1$ represents a hydrogen atom, an alkyl group, or a group represented by formula (b):

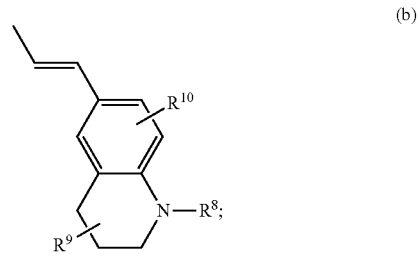

(b)

$R^2$ and $R^6$ are the same or different and each represent a hydrogen atom or a halogen atom;

$R^3$, $R^4$, $R^5$, and $R^7$ are the same or different and each represent a hydrogen atom, a halogen atom, or an alkyl group;

$R^8$ represents a hydrogen atom or —$(CH_2)_l$—$(Y)_m$—$(CH_2)_n$—Z wherein Y represents —CO—, —CONH—, or a triazole ring, Z represents a carboxyl group, a sulfonic acid group, or a —CO— peptide residue, l and n each represent an integer of 1 to 6, and m represents 0 or 1;

$R^9$ and $R^{10}$ are the same or different and each represent a hydrogen atom, an alkyl group, an alkoxy group, a halogen atom, an amino group, a nitro group, or a cyano group; and $R^8$ and $R^{10}$ together optionally form an alkylene group.

2. The boron-dipyrrin complex according to claim 1, wherein $X^1$ is a fluoro $C_1$-$C_4$ alkyl group.

3. The boron-dipyrrin complex according to claim 1, wherein one of $R^2$ and $R^6$ is a halogen atom and the other is a hydrogen atom or a halogen atom.

4. The boron-dipyrrin complex according to claim 1, wherein $R^1$ is the group represented by formula (b).

5. A boron-dipyrrin complex represented by formula (1A):

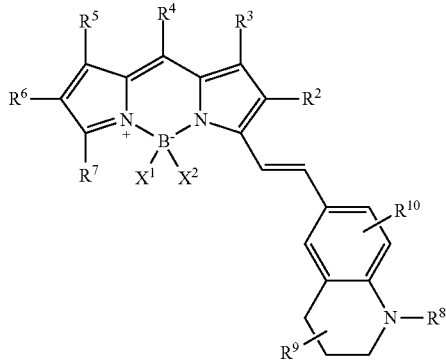

(1A)

wherein:
$X^1$ represents a halogenoalkyl group;
$X^2$ represents a halogen atom;
one of $R^2$ and $R^6$ represents a halogen atom and the other represents a hydrogen atom or a halogen atom;
$R^3$, $R^4$, $R^5$, and $R^7$ are the same or different and each represent a hydrogen atom, a halogen atom, or an alkyl group;
$R^8$ represents a hydrogen atom or —$(CH_2)_l$—$(Y)_m$—$(CH_2)_n$—Z wherein Y represents —CO—, —CONH—, or a triazole ring, Z represents a carboxyl group, a sulfonic acid group, or a —CO— peptide residue, l and n each represent an integer of 1 to 6, and m represents 0 or 1;
$R^9$ and $R^{10}$ are the same or different and each represent a hydrogen atom, an alkyl group, an alkoxy group, a halogen atom, an amino group, a nitro group, or a cyano group; and
$R^8$ and $R^{10}$ together optionally form an alkylene group.

6. The boron-dipyrrin complex according to claim 5, wherein $X^1$ is a fluoro $C_1$-$C_4$ alkyl group.

7. A medicament comprising, as an active ingredient, the boron-dipyrrin complex according to claim 5.

8. A pharmaceutical composition comprising:
the boron-dipyrrin complex according to claim 5; and
a pharmaceutically acceptable carrier.

9. A method for treating a disease selected from the group consisting of Alzheimer's disease, Parkinson's disease, diabetes mellitus, Huntington's disease, and systemic amyloidosis, comprising administering an effective amount of the boron-dipyrrin complex according to claim 5 to a subject in need thereof.

10. The method of claim 9, wherein the disease is Alzheimer's disease.

* * * * *

UNITED STATES PATENT AND TRADEMARK OFFICE
CERTIFICATE OF CORRECTION

PATENT NO. : 10,188,671 B2
APPLICATION NO. : 15/555721
DATED : January 29, 2019
INVENTOR(S) : Motomu Kanai et al.

Page 1 of 1

It is certified that error appears in the above-identified patent and that said Letters Patent is hereby corrected as shown below:

In the Claims

Claim 5, at Column 32, Line 9:
"in represents 0 or 1;"
Should read:
--m represents 0 or 1;--

Signed and Sealed this
Twenty-first Day of May, 2019

Andrei Iancu
*Director of the United States Patent and Trademark Office*